(12) United States Patent
Zheng et al.

(10) Patent No.: US 11,377,483 B2
(45) Date of Patent: Jul. 5, 2022

(54) SANDWICH ASSAY DESIGN FOR SMALL MOLECULES

(71) Applicant: Siemens Healthcare Diagnostics Inc., Tarrytown, NY (US)

(72) Inventors: Yi Feng Zheng, Wilmington, DE (US); Tie Q. Wei, Wilmington, DE (US); Manoj Sharma, Hockessin, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/247,219

(22) Filed: Dec. 4, 2020

(65) Prior Publication Data

US 2021/0087255 A1    Mar. 25, 2021

Related U.S. Application Data

(63) Continuation of application No. 15/536,296, filed as application No. PCT/US2015/065237 on Dec. 11, 2015, now abandoned.

(60) Provisional application No. 62/093,118, filed on Dec. 17, 2014.

(51) Int. Cl.
*C07K 16/00* (2006.01)
*G01N 33/94* (2006.01)
(Continued)

(52) U.S. Cl.
CPC .............. *C07K 16/00* (2013.01); *C07K 16/44* (2013.01); *G01N 33/566* (2013.01);
(Continued)

(58) Field of Classification Search
CPC ...... C07D 497/04; C07K 16/00; C07K 16/44; C07K 2317/10; C07K 2317/54; G01N 33/566; G01N 33/9493
See application file for complete search history.

(56) References Cited

U.S. PATENT DOCUMENTS 6,709,873 B1    3/2004  Yatscoff et al.
8,586,322 B2 *  11/2013 Wei .................... G01N 33/9493
                                                        435/7.94
(Continued)

FOREIGN PATENT DOCUMENTS

WO         0022000       4/2000
WO      2008082982       5/2008
WO     20140888987       6/2014

OTHER PUBLICATIONS

Szurdoki et al; "Important Factors in Hapten Design and Enzyme-Linked Immunosorbent Assay Development"; in Immunoanalysis of Agrochemicals; ACS Symposium Series; vol. 586; Chapter 4; pp. 39-63; 1995.

(Continued)

*Primary Examiner* — Galina M. Yakovleva

(57) ABSTRACT

Methods are disclosed of designing antibodies for a sandwich assay for a small molecule having a molecular weight of about 500 to about 2,000. The method comprises preparing a first antibody that binds to the small molecule, and preparing a second antibody that binds to the small molecule at a portion of the small molecule other than a portion to which the first antibody binds. The second antibody is prepared from an immunogen that comprises a predetermined portion of the small molecule. The antibodies may be employed in sandwich assays for the small molecule.

13 Claims, 10 Drawing Sheets

(51) Int. Cl.
*G01N 33/566* (2006.01)
*C07K 16/44* (2006.01)
*C07D 497/04* (2006.01)

(52) U.S. Cl.
CPC ....... *G01N 33/9493* (2013.01); *C07D 497/04* (2013.01); *C07K 2317/10* (2013.01); *C07K 2317/54* (2013.01)

(56) References Cited

U.S. PATENT DOCUMENTS

| | | | |
|---|---|---|---|
| 2004/0198953 | A1 | 7/2004 | Yatscoff et al. |
| 2006/0099654 | A1 | 11/2006 | Huster |
| 2006/0246518 | A1* | 11/2006 | Chen ...................... C07K 16/44 435/7.5 |
| 2013/0236918 | A1 | 12/2013 | Wei |
| 2014/0154706 | A1 | 6/2014 | Zheng et al. |
| 2018/3606828 | | 10/2018 | Wei |
| 2021/0199677 | A1* | 7/2021 | Wei ...................... G01N 33/531 |

OTHER PUBLICATIONS

Goodrow et al; "Strategies for Immunoassay Hapten Design"; in Immunoanalysis of Agrochemicals; ACS Symposium Series; vol. 586; Chapter 9; pp. 119-139; 1995.

Ocain et al., "A Nonimmunosuppressive Triene-Modified Rapamycin Analog is a Potent Inhibitor of Peptidyl Prolyl Cis-Trans-Isomerase", May 14, 1993, Biochemical and Biophysical Research Communications, Elsevier, Amsterdam, NL, vol. 192, No. 3, pp. 1340-1346.

European Search Report and Written Opinion of European Application No. 15870760.4 dated Feb. 12, 2018.

Gounden et al., "Tacrolimus Measurement: Building a Better Immunoassay", Jan. 10, 2014 (Jan. 10, 2014), Clinical Chemistry, vol. 60, No. 4, pp. 575-576.

European Office Action of European Application No. 15870760.4 dated May 22, 2019.

International Search Report and Written Opinion of International Application No. PCT/US2015/065237 dated Apr. 8, 2016.

Quinton et al., "Toward the Limits of Sandwich Immunoassay of Very Low Molecular Weight Molecules", Mar. 15, 2010, Analytical Chemistry, vol. 82, No. 6, pp. 2536-2540.

Wei et al., "Sandwich Assay for Tacrolimus Using 2 Anti-Tacrolimus Antibodies", 2014, Clinical Chemistry 60:4, pp. 1-10.

Response to European Examination Report for EP 15870760.4, dated Sep. 11, 2018.

Response to European Examination Report for EP 15870760.4, dated Oct. 1, 2019.

Summons to Oral Proceedings for EP 15870760.4, dated May 15, 2020.

Minutes of Oral Proceedings for EP 15870760.4, dated Oct. 23, 2020.

* cited by examiner

I
Sirolimus

VIa ⟶

+

SANDWICH ASSAY DESIGN FOR SMALL MOLECULES

CROSS REFERENCE TO RELATED APPLICATIONS/INCORPORATION BY REFERENCE STATEMENT

The subject application is a continuation of U.S. Ser. No. 15/536,296, filed Jun. 15, 2017; which is a US national stage application filed under 35 USC § 371 of International Application No. PCT/US2015/65237, filed Dec. 11, 2015; which claims benefit under 35 USC § 119(e) of provisional application U.S. Ser. No. 62/093,118, filed Dec. 17, 2014. The entire contents of each of the above-referenced patents/patent applications are hereby expressly incorporated herein by reference.

BACKGROUND

The present disclosure relates to compounds, methods and kits for the determination of small molecules, in samples, such as patient samples, known or suspected to contain one or more of such small molecules. In some aspects the present disclosure relates to sandwich assays for small molecules such as, for example, immunosuppressant drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are therapeutic drugs that are carefully administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus.

Two most commonly administered immunosuppressive drugs to prevent organ rejection in transplant patients are cyclosporine (CSA) and FK-506 (FK or tacrolimus). Another drug that finds use as an immunosuppressant in the United States and other countries is sirolimus, also known as rapamycin. Derivatives of sirolimus are also useful as immunosuppressants. Such derivatives include, for example, everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because distribution and metabolism of an immunosuppressant drug can vary greatly between patients and because of a wide range and severity of adverse reactions, accurate monitoring of the drug level is essential.

There is, therefore, a continuing need to develop fast and accurate diagnostic methods to measure levels of small molecules such as, for example, immunosuppressant drugs or derivatives thereof in patients. The methods should be capable of being fully automated and should selectively detect the parent molecule while minimizing inaccuracies resulting from the cross-reactivity of its metabolites or from constituents in a sample suspected of containing the small molecule.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION

Figure 1:
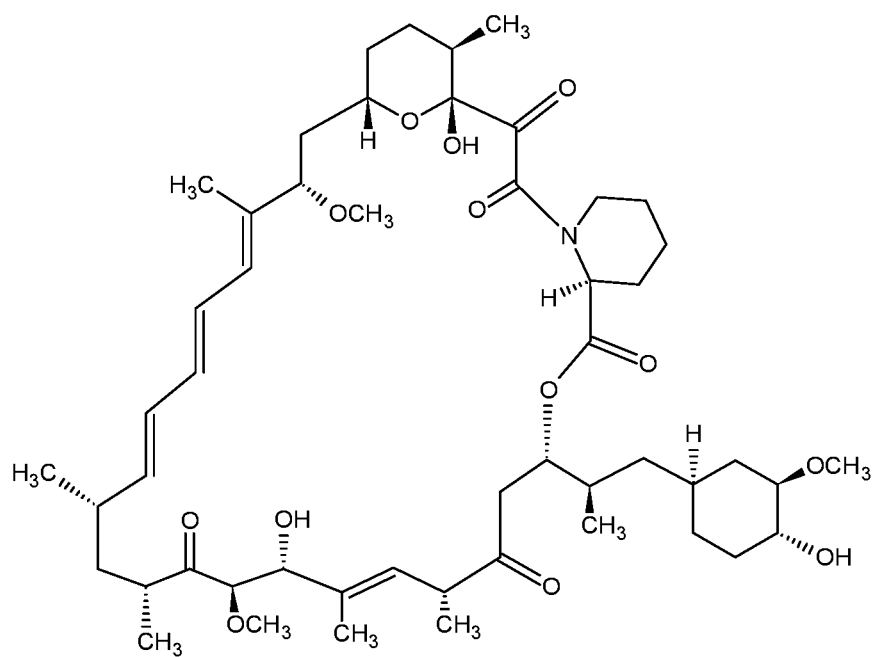
FIG. 1 is a chemical formula for sirolimus (I).

Some examples in accordance with the principles described herein are directed to methods of designing antibodies for a sandwich assay for a small molecule having a molecular weight of about 500 to about 2,000. The method comprises preparing a first antibody that binds to the small molecule, and preparing a second antibody that binds to the small molecule at a portion of the small molecule other than a portion to which the first antibody binds. The second antibody is prepared from an immunogen that comprises a predetermined portion of the small molecule.

Some examples in accordance with the principles described herein are directed to methods of determining a presence and/or amount of a small molecule having a molecular weight of about 500 to about 2,000 in a sample suspected of containing the small molecule. The sample, a first antibody for the small molecule as described above, and a second antibody for the small molecule as described above are provided in combination in a medium, which is incubated under conditions for binding of the first antibody and the second antibody to the small molecule. The medium is examined for the presence of an immunocomplex comprising the small molecule, the first antibody and the second antibody, the presence and/or amount of the immunocomplex indicating the presence and/or amount of the small molecule in the sample.

Some examples in accordance with the principles described herein are directed to methods of designing antibodies for a sandwich assay for a small molecule having a molecular weight of about 500 to about 2,000. A first monoclonal antibody that binds to a portion of the small molecule is prepared. A second monoclonal antibody that binds to the small molecule at a portion of the small molecule other than the portion to which the first monoclonal antibody binds is also prepared from an immunogen that comprises the small molecule that is derivatized at the portion of the small molecule to which the first monoclonal antibody binds. The antibodies may be employed in methods of determining a presence and/or amount of a small molecule having a molecular weight of about 500 to about 2,000 in a sample suspected of containing the small molecule.

Some examples in accordance with the principles described herein are directed to methods of designing antibodies for a sandwich assay for sirolimus. A first monoclonal antibody that binds to sirolimus is prepared. A second monoclonal antibody that binds to sirolimus at a portion of sirolimus other than the portion to which the first monoclonal antibody binds is also prepared from an immunogen that is derivatized at the portion of sirolimus to which the first antibody binds. The antibodies may be employed in methods of determining a presence and/or amount of sirolimus in a sample suspected of containing sirolimus.

The present inventors have discovered that monoclonal antibodies can be designed that specifically bind simultaneously to separate portions of small molecules. This discovery is surprising because small molecules are haptens, which are relatively small molecules (molecular weight (daltons) less than about 2000, or less than about 1500, or less than about 1000) and are not considered to have more than one site to which an antibody can bind. In accordance with the principles described herein, at least two different antibodies can be prepared, which bind to separate portions of a small molecule at the same time.

The term "small molecule" refers to a molecule having a molecular weight of about 150 to about 2,000, or about 150 to about 1,500, or about 150 to about 1,000, or about 150 to about 500, or about 300 to about 2,000, or about 300 to about 1,500, or about 300 to about 1,000, or about 500 to about 2,000, or about 500 to about 1,500, or about 500 to about 1,000, for example. For the most part, small molecules, which are sometimes referred to as haptens, do not elicit an immune response unless linked to large molecule or immunogenic carrier that does illicit an immune response in order to raise antibodies. Haptens are compounds capable of binding specifically to corresponding antibodies, but do not themselves act as immunogens (or antigens) for preparation of the antibodies.

The phrase "antibody for a small molecule" refers to an antibody that binds specifically to the small molecule and does not bind to any significant degree to other substances that would distort the analysis for the small molecule. Furthermore, the antibody for the small molecule binds specifically to a certain domain of the small molecule. Specific binding involves the specific recognition of one of two different molecules, or two different domains of a small molecule, for the other compared to substantially less recognition of other molecules or other domains of a small molecule. On the other hand, non-specific binding involves non-covalent binding between molecules that is relatively independent of specific surface structures. Non-specific binding may result from several factors including hydrophobic interactions between molecules.

A small molecule, to which examples in accordance with the principles described herein may be applied, has spatially separate binding domains for the antibodies. The small molecule may be linear or it may comprise one or more rings, for example, two rings, or three rings, or four rings, or five rings, or more. The binding domains on the small molecule should be separated such that two different antibodies can bind simultaneously to the small molecule without interfering with the binding of each other to form a three-member complex (or immunocomplex) wherein each antibody binds to an extent necessary so that a sufficiently stable complex is formed comprising the two antibodies and the small molecule. The complex is considered sufficiently stable when the complex remains intact during an assay so that the complex can be detected and the amount of the complex accurately reflects the amount of a small molecule analyte in a sample. The stable complex permits an accurate and sensitive assay for the small molecule analyte. In some examples, the binding domains for the different antibodies on a linear small molecule should be separated by at least 5 carbon atoms, or at least 6 carbon atoms, or at least 7 carbon atoms, or at least 8 carbon atoms, or at least 9 carbon atoms, or at least 10 carbon atoms, for example. In some examples, the binding domains for the different antibodies on a small molecule that comprises one or more rings should be separated by at least 3 carbon atoms, or at least 4 carbon atoms, or at least 5 carbon atoms, or at least 6 carbon atoms, or at least 7 carbon atoms, or at least 8 carbon atoms, for example.

In some examples the small molecule comprises at least one large ring, which is a 15-50 membered ring, or a 15-45 membered ring, or a 15-40 membered ring, or a 15-35 membered ring, or a 15-30 membered ring, or a 15-25 membered ring, or a 15-20 membered ring, or a 20-50 membered ring, or a 20-45 membered ring, or a 20-40 membered ring, or a 20-35 membered ring, or a 20-30 membered ring, or a 20-25 membered ring, or a 25-50 membered ring, or a 25-45 membered ring, or a 25-40 membered ring, or a 25-35 membered ring, or a 25-30 membered ring, or a 30-50 membered ring, or a 30-45 membered ring, or a 30-40 membered ring, for example. The atoms forming the ring are primarily carbon and may also include, but are not limited to, oxygen, nitrogen and sulfur, for example. The large ring may also comprise 1-5, or 1-4, or 1-3 or 1-2, or 2-5, or 2-4, or 2-3, small rings, which are 5-7 membered rings or 5-6 membered rings. Some of the atoms of the small rings may be part of the large ring.

In some examples, the small molecule comprises a three dimensional conformation with one or more unique chemical functional groups that allow different antibodies to be prepared where at least two different antibodies can approach and bind to different binding domains on the small molecule without interfering with one another. The unique chemical functional groups include, byway of illustration and not limitation, carbon-carbon double bonds, carbon-carbon triple bonds, carbonyl groups, imine groups, carboxyl groups, hydroxyl groups, amine groups, amide groups, ester groups and ether groups, for example, and combinations of two or more of the above. The chemical functional groups may be unconjugated or conjugated. The term "conjugated" refers to contiguous atoms that have available p-orbitals such that electrons can be delocalized over the contiguous atoms. Examples of conjugated atoms include, but are not limited to, one, two, three, four, or five or more conjugated carbon-carbon double bonds (vinyl groups); one, two, three, four, or five or more conjugated carbon-carbon triple bonds; a combination of one, two, three, four, or five or more conjugated carbon-carbon double bonds, carbon-carbon triple bonds, imine groups, carbonyl groups, and anions, for example. In some examples, the chemical functional groups provide a particular spatial conformation for the small molecule.

The chemical functional groups serve at least two purposes in accordance with the principles described herein. They may be employed to prepare a first antibody that specifically binds to a binding domain of the small molecule at which the chemical functional group is located. In addition, they may be employed for modification of the small molecule at the area of the small molecule comprising the chemical functional group and using the modified small molecule as part of an immunogen to raise a second antibody against a binding domain other than the binding domain to which the first antibody binds. In some examples, modification of the area of the small molecule comprising the chemical functional group alters a three dimensional conformation of the area to further promote the formation of antibodies at binding domains of the small molecule other than the area comprising the chemical functional group.

In some examples the small molecule is a macrolide. In some examples the macrolide is an immunosuppressant drug. The term "immunosuppressant drugs" includes those that act on immunophilin such as, but not limited to, cyclosporin (including cyclosporin A, cyclosporin B, cyclosporin C, cyclosporin D, cyclosporin E, cyclosporin F, cyclosporin G, cyclosporin H, cyclosporin I), tacrolimus (FR-900506, FK506, PROGRAF®), sirolimus (rapamycin, RAPAMUNE®), and derivatives of the above such as, but not limited to, Everolimus (RAD, CERTICAN®), for example.

As mentioned above, some examples in accordance with the principles described herein are directed to methods of designing antibodies for a sandwich assay for a small molecule having a molecular weight of about 500 to about 2,000. The method comprises preparing a first antibody that binds to a portion or domain of the small molecule, and preparing a second antibody that binds to the small molecule at a portion or domain of the small molecule other than a portion or domain to which the first antibody binds. The second antibody is prepared from an immunogen that comprises a predetermined portion or domain of the small molecule.

The phrase "immunogen that comprises a predetermined portion or domain of the small molecule" refers to a compound that comprises a portion of the small molecule other than the portion of the small molecule to which the first antibody binds. The compound may be the small molecule that has been modified to enhance the ability of preparing an antibody that binds to a portion of the small molecule other than the portion to which the first antibody binds. On the other hand, the compound may be a compound other than the small molecule that comprises the portion of the small molecule other than the portion to which the first antibody binds. In some examples, the predetermined portion of the small molecule is obtained by modification of the small molecule to alter a spatial conformation of the small molecule. In some examples, the predetermined portion of the small molecule is a compound that consists essentially of the predetermined portion. In either case, the compound is linked to an immunogenic carrier for use in preparing antibodies in accordance with the principles described herein.

Preparation of monoclonal antibodies that simultaneously bind to two different domains on a small molecule enables the use of such antibodies in sandwich assays in which the small molecule is simultaneously bound by the two different antibodies to form an immunocomplex. The ability to perform sandwich assays on small molecules enhances the sensitivity of an assay for the small molecule. In addition, in the case of sandwich assays involving one monoclonal antibody bound to a support, the assay may be conducted in the presence of impurities and interfering substances of a sample because the support can be separated from the sample and washed after small molecule has been allowed to bind to the monoclonal antibody of the support but before introduction of the second monoclonal antibody.

Antibodies may include a complete immunoglobulin or fragment thereof, which immunoglobulins include the various classes and isotypes, such as IgA, IgD, IgE and IgM, for example. Fragments thereof may include Fab, Fv and F(ab')$_2$, Fab', for example. In addition, aggregates, polymers, and conjugates of immunoglobulins or their fragments can be used where appropriate so long as binding affinity for a particular molecule is maintained.

Antibodies in accordance with the principles described herein may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

Monoclonal antibodies can be prepared by techniques that are well known in the art such as preparing continuous hybrid cell lines and collecting the secreted protein (somatic cell hybridization techniques). Monoclonal antibodies may be produced according to the standard techniques of Köhler and Milstein, Nature 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with an immunogen in accordance with the principles described herein. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as enzyme-linked immunosorbent assay (ELISA) or other immunoassays appropriate for screening.

An antibody (prepared from an immunogen in accordance with the principles described herein) with the requisite specificity may be selected by screening methodologies, which include, by way of illustration and not limitation, ELISA, dot blots, Western analysis, and Surface Plasmon Resonance, for example. In this manner an antibody is obtained that binds to a domain of a small molecule of interest and does not bind to any detectable degree to other domains of the small molecule or to other molecules that are not of interest in a particular assay. In some examples in accordance with the principles described herein, an antibody that binds to a domain of a small molecule of interest has a binding affinity for the domain of the small molecule of interest of about $10^7$ to about $10^{14}$ liters/mole, or about $10^7$ to about $10^{11}$ liters/mole, or about $10^7$ to about $10^{12}$ liters/mole, or about $10^8$ to about $10^{14}$ liters/mole, or about $10^8$ to about $10^{11}$ liters/mole, or about $10^8$ to about $10^{12}$ liters/mole, for example. The phrase "any detectable degree" means that the antibody that specifically binds to a domain of a small molecule of interest has a binding affinity for other domains of the small molecule of interest or for other molecules that are not of interest of less than about $10^4$ liters/mole, or less than about $10^3$ liters/mole, or less than about $10^2$ liters/mole, or less than about 10 liters/mole, for example.

The term "immunogenic carrier" means a group or moiety which, when conjugated to a hapten and injected into a mammal or otherwise employed as an immunogen, induces an immune response and elicits production of antibodies that bind to the hapten. Immunogenic carriers are also sometimes referred to as antigenic carriers. In some examples in accordance with the principles described herein, immunogens comprising immunogenic carriers, including poly(amino acid) and non-poly(amino acid) immunogenic carriers, linked to a small molecule at a particular position are synthesized and used to prepare antibodies in accordance with the principles described herein.

The molecular weight range (in Daltons) for poly(amino acids) that are immunogenic carriers is about 5,000 to about 10,000,000, or about 20,000 to about 600,000, or about 25,000 to about 250,000 molecular weight, for example. Poly(amino acid) immunogenic carriers include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), thyroglobulin, ovalbumin or fibrinogen, for example. In one illustrative example, the protein is KLH; in another illustrative example, the protein is BSA. Non-poly(amino acid) immunogenic carriers include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

As mentioned above, in some examples in accordance with the principles described herein, the immunogenic carrier may be linked to the small molecule at a predetermined position on the small molecule by means of a linking group. In some examples, the linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to the small molecule such as, but not limited to, an amino acid residue on a poly(amino acid), for example. In some examples, the linking group comprises an oxime functionality.

The number of heteroatoms in the linking group may be in the range from 0 to about 20, or 1 to about 15, or about 2 to about 10. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

Sirolimus as a Specific Example

The following specific description is by way of illustration of, and not as a limitation on, the scope of the present disclosure. Selection of immunosuppressant drugs, and sirolimus in particular, is also by way of illustration and not limitation as the present disclosure has general application to detection of any small molecule that has spatially separated regions to which antibodies can be raised and to which such raised antibodies will bind specifically during an assay for the compound.

Monoclonal antibodies may be prepared that bind to separate portions of the sirolimus molecule (FIG. 1). The separate portions to which the monoclonal antibodies bind may be determined, for example, by cross-reactivity studies using, for example, metabolites of sirolimus, or modified sirolimus.

Figure 2:
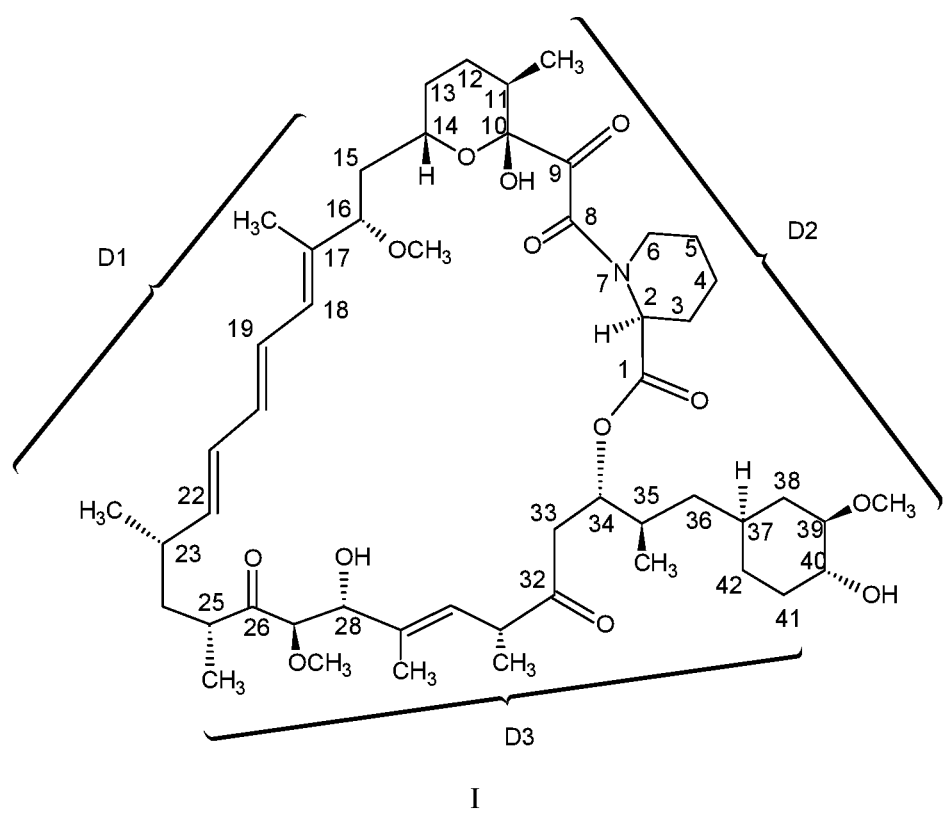
FIG. 2 is the chemical formula of FIG. 1 with numbering and depicting portions of the molecule to which monoclonal antibodies can be prepared in accordance with the principles described herein.

Referring to FIG. 2, by way of illustration and not limitation, three potential binding domains on the sirolimus molecule are indicated as D1, D2 and D3. Binding domain D1 extends approximately from ring atom 15 to ring atom 21 and includes a triene moiety from ring atom 17 to ring atom 22. Binding domain D2 extends approximately from the methyl group on atom 11 to the methoxy group on atom 39. Binding domain D3 extends from the methyl group on ring atom 25 to atom 41. In one example in accordance with the principles described herein, a first antibody is prepared that binds to D1 of the sirolimus molecule. A second antibody is prepared that binds to sirolimus at a portion of the small molecule other than a portion to which the first antibody binds, which in this example is either domain D2 or domain D3 of the sirolimus molecule. The second antibody is prepared from an immunogen that comprises a predetermined portion of the small molecule.

In one example the predetermined portion of the sirolimus molecule is obtained by modification of the sirolimus molecule to alter a spatial conformation of the sirolimus molecule. In the example shown by way of illustration and not limitation (FIG. 3), the sirolimus molecule is modified in the triene area (D1) to yield modified sirolimus compound IIA or IIB, or a mixture thereof, which, when linked to an immunogenic carrier, may be used to prepare an immunogen to raise antibodies that bind specifically to D2 or D3 of I.

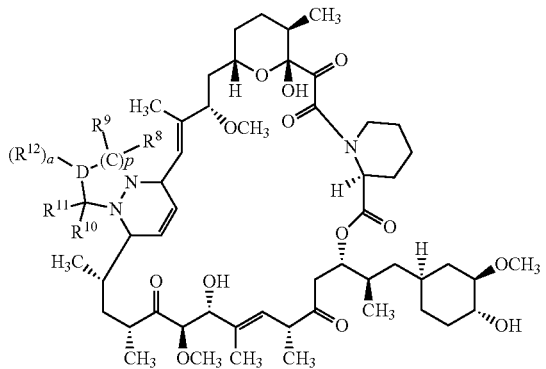

IIA or

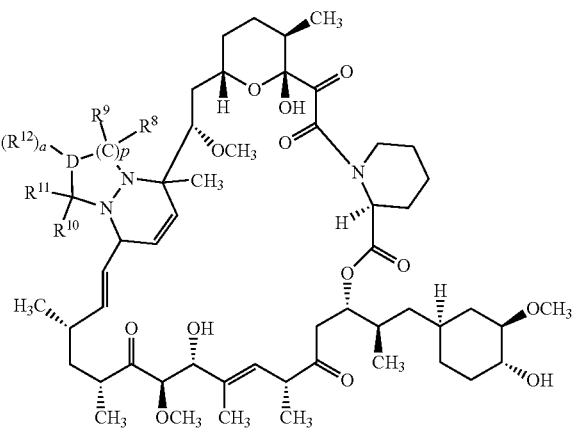

IIB wherein:

$R^8$ and $R^9$ are each independently H, non-bulky organic radical or a bulky organic radical, or are taken together to form a double bond to O or $CH_2$;

$R^{10}$ and $R^{11}$ are each independently H, non-bulky organic radical or a bulky organic radical, or are taken together to form a double bond to O or $CH_2$;

$R^{12}$ is H, non-bulky hydrocarbyl, or a bulky organic radical;

wherein, in one example in accordance with the principles described herein, at least one of $R^8$, $R^9$, $R^{10}$, $R^{11}$ or $R^{12}$ is a bulky organic radical;

p is 1, 2 or 3;

a is 0 or 1; and

D is N, O, or CH, with the proviso that a is 0 when D is O.

The term "hydrocarbyl" refers to an organic radical that consists solely of carbon and hydrogen. A hydrocarbyl group may be unsaturated or it may contain one or more carbon-carbon double bonds or one or more carbon-carbon triple bonds or a mixture thereof. The term "hydrocarbyl" includes alkyl, alkenyl and alkynyl.

The phrase "bulky organic radical" refers to an organic radical that exhibits a large molecular size for its weight. The bulky organic radical hinders the ability of a specific binding member to bind to an area of a molecule that comprises the bulky organic radical. The phrase "bulky hydrocarbyl" refers to a hydrocarbyl group that exhibits a large molecular size for its weight such as, for example, that exhibited by an alkyl group that is branched or cyclic.

The phrase "non-bulky organic radical" refers to an organic radical that does not exhibit a large molecular size for its weight. The non-bulky organic radical does not hinder to a significant degree the ability of an antibody to bind to an area of a molecule that comprises the non-bulky organic radical. The phrase "non-bulky hydrocarbyl" refers to a hydrocarbyl group that does not exhibit a large molecular size for its weight such as that exhibited by a straight chain alkyl group.

The term "alkyl" refers to an organic radical that consists solely of single-bonded carbon and hydrogen in either a straight, branched, or cyclic configuration. The number of carbon atoms in the organic radical is 1 to 50, or 1 to 40, or 1 to 30, or 1 to 25, or 1 to 20, or 1 to 15, or 1 to 10, or 1 to 5, or 2 to 50, or 2 to 40, or 2 to 30, or 2 to 25, or 2 to 20, or 2 to 15, or 2 to 10, or 2 to 5, or 5 to 50, or 5 to 40, or 5 to 30, or 5 to 25, or 5 to 20, or 5 to 15, or 5 to 10. The term "lower alkyl" refers to alkyl wherein the number of carbon atoms in the organic radical is 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10.

Bulky hydrocarbyl includes branched chain hydrocarbyl and cyclic hydrocarbyl. Bulky branched chain hydrocarbyl has branching at or near the carbon atom that is attached to another molecule. Examples of bulky branched chain alkyl include, but are not limited to, sec-butyl, tert-butyl, triethylmethyl, diethylmethyl, tripropylmethyl and dipropylmethyl, for example. Cyclic alkyl is alkyl comprising one or more rings. Examples of cyclic alkyl include, but are not limited to, cyclopropyl, cyclobutyl, cyclopentyl, cyclohexyl, cycloheptyl and norbornyl, for example. Examples of non-bulky alkyl include, but are not limited to, methyl, ethyl, propyl, butyl, pentyl, hexyl, heptyl and octyl, for example.

The term "alkenyl" refers to a hydrocarbyl group having hydrocarbon chains of the number of carbon atoms specified above of either a straight- or branched-configuration and having at least one carbon-carbon double bond, which may occur at any point along the hydrocarbon chain, examples of which include, but are not limited to, ethenyl, propenyl, butenyl, pentenyl, dimethyl pentenyl, for example.

The term "alkynyl" refers to a hydrocarbyl group having hydrocarbon chains of the number of carbon atoms specified above containing at least one carbon-carbon triple bond, including, but not limited to, ethynyl, 1-propynyl, 2-propynyl, 1-butynyl, and 2-butynyl, for example.

The term "lower hydrocarbyloxy" refers to a hydrocarbyl group that is an organic radical of the number of carbon atoms designated above of either a straight, branched or cyclic configuration wherein the organic radical includes an ether oxygen for linking a hydrocarbyl group to a parent compound.

The term "lower alkoxy" refers to an organic radical of the number of carbon atoms designated above of either a straight, branched or cyclic configuration wherein the organic radical includes an ether oxygen for linking an alkyl group to a parent compound.

As used herein, the term "aryl" refers to an organic radical derived from an aromatic hydrocarbon by the removal of one atom and containing one or more aromatic rings such as, but not limited to, 1 to 5 aromatic rings, or 1 to 4 aromatic rings, or 1 to 3 aromatic rings, or 1 to 2 aromatic rings, or 2 to 4 aromatic rings, or 2 to 3 aromatic rings, for example. Examples of aryl include, but are not limited to, phenyl (from benzene), naphthyl (from naphthalene), and anthracyl (from anthracene), for example. The aryl radical may be substituted or unsubstituted. "Substituted aryl" refers to aryl groups that comprise one or more substituents such as, but not limited to, a bulky hydrocarbyl, a non-bulky hydrocarbyl, a functional group (e.g., chloro, bromo, iodo, fluoro, nitro and sulfone), for example.

As used herein, "arylhydrocarbyl" refers to an organic radical having a lower hydrocarbyl group to which is attached an aryl group. As used herein, "aralkyl" refers to an organic radical having a lower alkyl group to which is attached an aryl group such as, but not limited to, benzyl, phenethyl, 3-phenylpropyl and 1-naphthylethyl, for example.

An immunogenic carrier may be linked to IIA or IIB or both through a substituent at ring atom 26 or a substituent at ring atom 32, or both, employing a linking group such as that described above. In one example, an oxime functionality may be formed from the carbonyl group at ring atom 26 or the carbonyl at ring atom 32, or both. The linking group for linking to an immunogenic carrier may be introduced into I either prior to or after modification of I at the triene functionality. In another example, one of $R^8$, $R^9$, $R^{10}$, $R^{11}$ or $R^{12}$ can be modified to incorporate a linking group for linking an immunogenic carrier to the modified sirolimus molecule.

In one example the predetermined portion of the sirolimus molecule is obtained by modification of the sirolimus molecule to alter a spatial conformation of the sirolimus molecule. In the example shown by way of illustration and not limitation, the sirolimus molecule is modified in the triene area (D1) with 4-phenyl-1,2,4-triazole-3,5-dione (PTAD) to yield modified sirolimus compound IIIA or IIIB (FIG. 4), or a mixture thereof, which, when linked to an immunogenic carrier, may be used to prepare an immunogen to raise antibodies that bind specifically to D2 or D3 of sirolimus (I).

IIIA

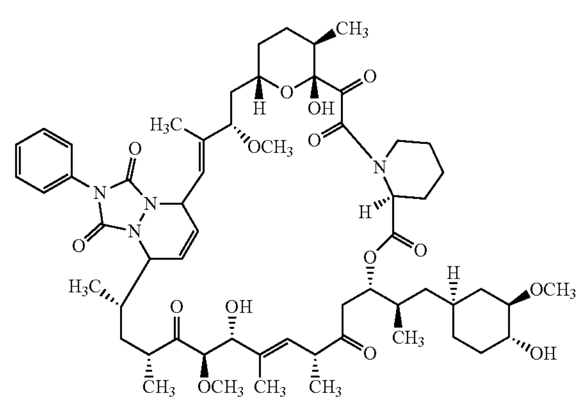

IIIB

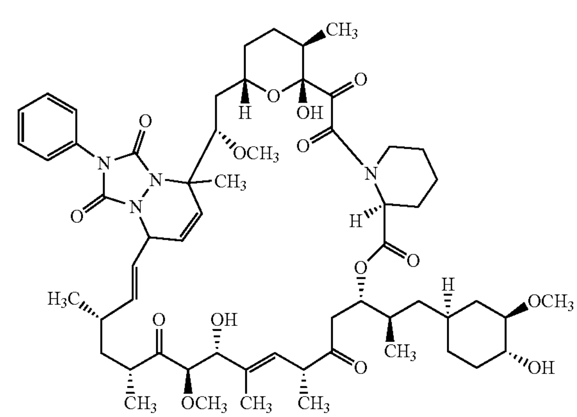

Similar to the discussion above with respect to IIA and IIB, an immunogenic carrier may be linked to IIIA or IIB or both through a substituent at ring atom 26 or a substituent at ring atom 32, or both, employing a linking group such as that described above. In one example, an oxime functionality may be formed from the carbonyl group at ring atom 26 or the carbonyl group at ring atom 32, or both. The linking group for linking to an immunogenic carrier may be introduced into I either prior to or after modification of I at the triene functionality. In another example, one of $R^8$, $R^9$, $R^{10}$, $R^{11}$ or $R^{12}$ is a functionality that may be modified to incorporate a linking group for linking an immunogenic carrier to the modified sirolimus molecule.

Preparation of Compounds

Figure 3:
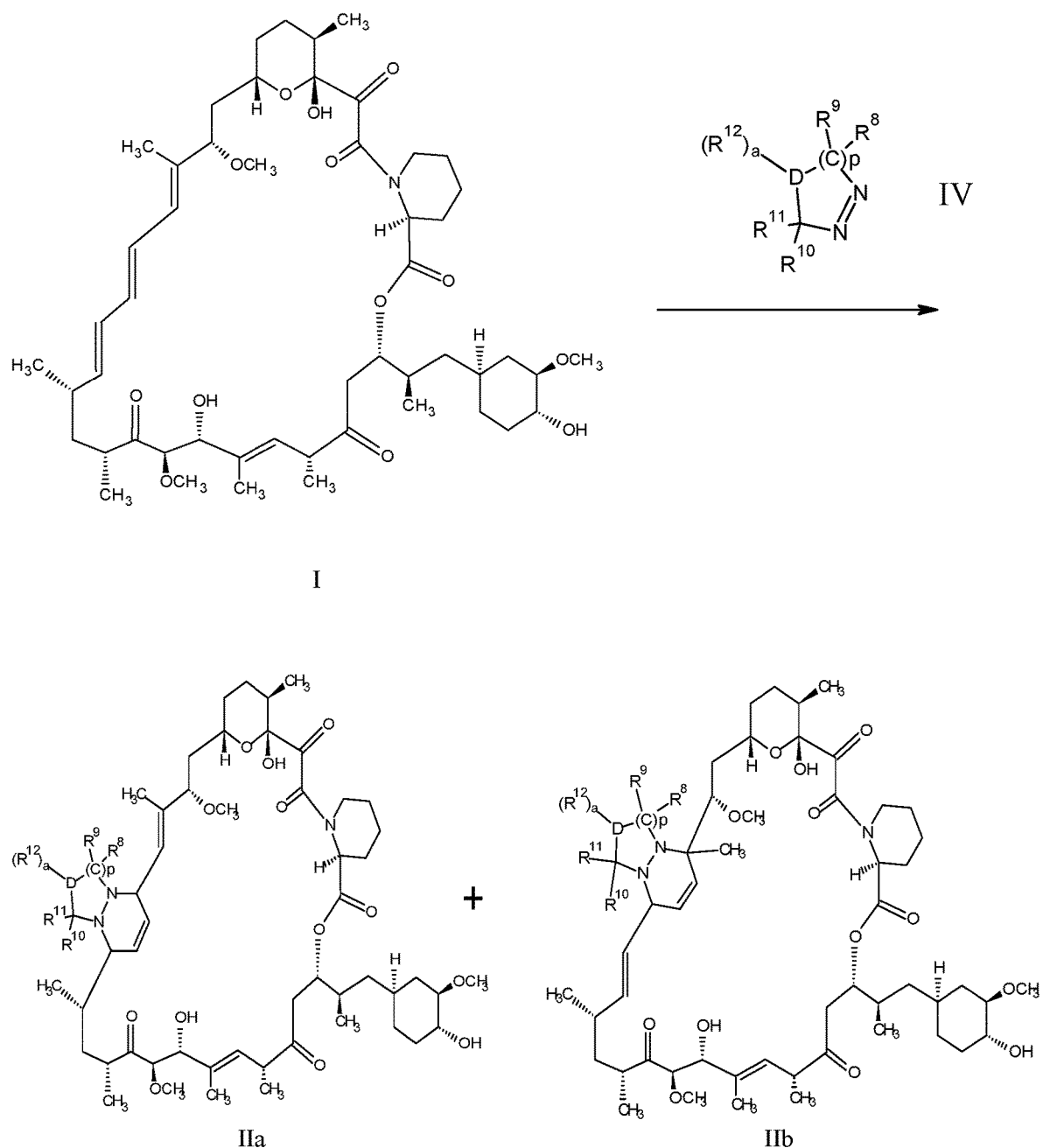
FIG. 3 is a reaction scheme for the preparation of adducts at the triene area of sirolimus in an example in accordance with the principles described herein.

Examples of methods of preparing compounds for preparation of antibodies in accordance with the principles described herein are described, by way of illustration and not limitation, with reference to FIG. 3. Other approaches may be employed to form the compounds consistent with the principles described herein. Referring to FIG. 3, sirolimus (I) is combined with cyclic reagent IV under conditions for carrying out a Diels-Alder addition reaction. The conditions include using an anhydrous non-polar organic medium such as, but not limited to, methylene chloride, toluene, hexane, nitrobenzene and carbon tetrachloride, for example; or a polar organic medium such as, but not limited to, ethanol, acetonitrile and phosphonium tosylates, and aqueous mixtures thereof, for example. The reaction is conducted at a temperature of about 15° C. to about 40° C., or about 20° C. to about 30° C., or about room temperature (about 22° C. to about 24° C.) for a period of about 15 minutes to about 45 minutes or about 30 minutes and then at a temperature of about 50° C. to about 100° C., or about 50° C. to about 80° C., or about the reflux temperature of the non-polar organic solvent for a period of about 30 minutes to about 90 minutes, or about 45 minutes to about 75 minutes, or about 60 minutes. The resulting product is purified by one or more techniques such as, but not limited to, evaporation, recrystallization, and chromatography such as, for example, thin layer chromatography (TLC), high performance liquid chromatography (HPLC), reverse phase liquid chromatography (RPLC), high turbulence liquid chromatography (HTLC), gas chromatography, for example. The product is a mixture of two isomers represented by compounds IIA and IIB in FIG. 3, which may be employed together or may be separated by one or more techniques for separating positional isomers such as, but not limited to, liquid chromatography (TLC, HPLC, RPLC, HTLC), and gas chromatography, for example.

Figure 4:
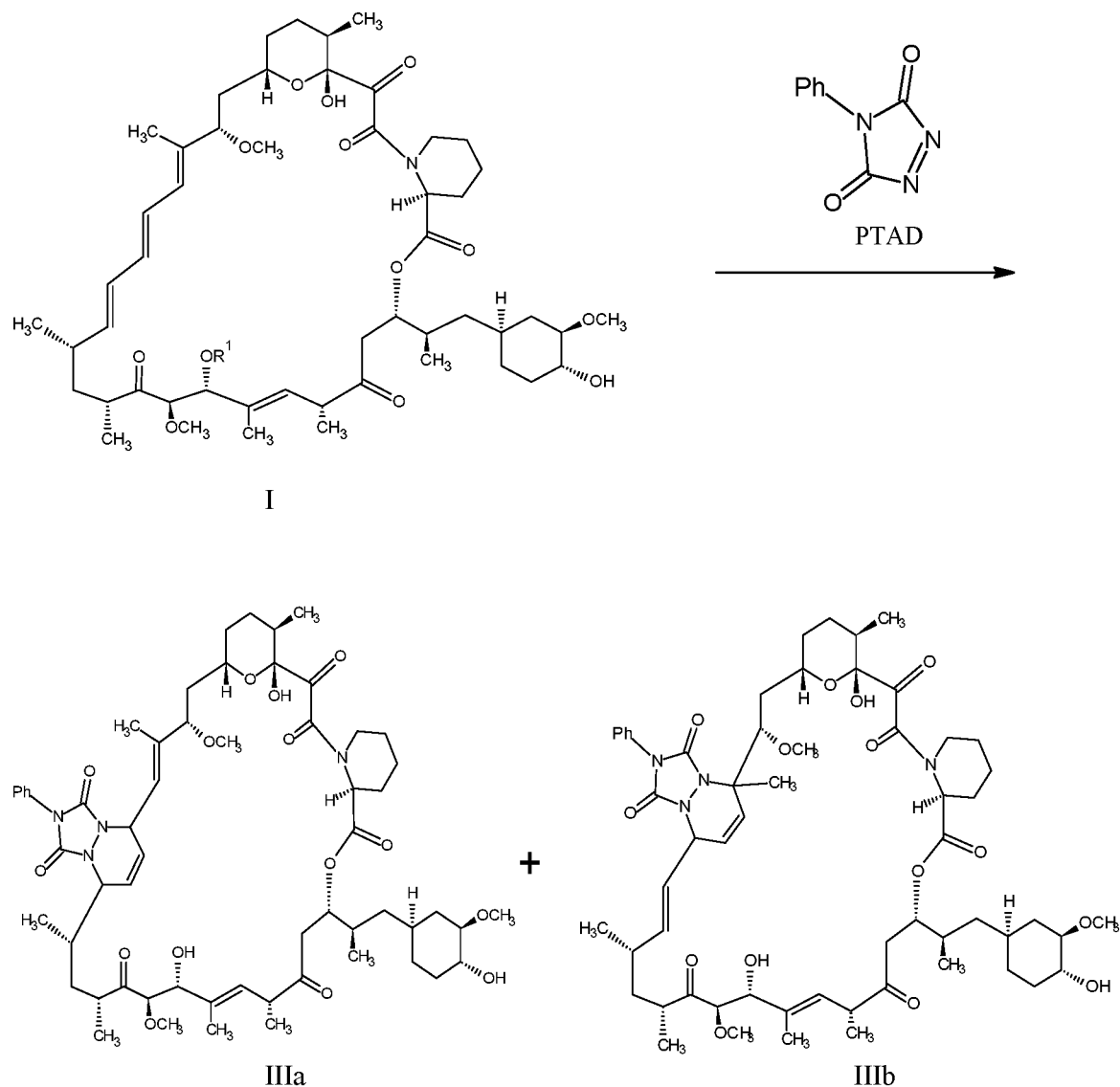
FIG. 4 is a reaction scheme for the preparation of a PTAD adduct at the triene area of sirolimus in another example in accordance with the principles described herein.

A particular example of a method of preparing compounds in accordance with the principles described herein is described, by way of illustration and not limitation, with reference to FIG. 4. Other approaches may be employed to form the compounds consistent with the principles described herein. Referring to FIG. 4, sirolimus (I) is combined with cyclic reagent PTAD under conditions for carrying out a Diels-Alder addition reaction. The conditions include using an anhydrous non-polar organic medium such as, but not limited to, methylene chloride, toluene, hexane, nitrobenzene and carbon tetrachloride, for example; or a polar organic medium such as, but not limited to, ethanol, acetonitrile and phosphonium tosylates, and aqueous mixtures thereof, for example. The reaction is conducted at a temperature of about 15° C. to about 40° C., or about 20° C. to about 30° C., or about room temperature (about 22° C. to about 24° C.) for a period of about 15 minutes to about 45 minutes or about 30 minutes and then at a temperature of about 50° C. to about 100° C., or about 50° C. to about 80° C., or about the reflux temperature of the non-polar organic solvent for a period of about 30 minutes to about 90 minutes, or about 45 minutes to about 75 minutes, or about 60 minutes. The resulting product is purified by one or more techniques such as, but not limited to, evaporation, liquid chromatography such as, for example, TLC, HPLC, RPLC, and HTLC, and gas chromatography, for example. The product is a mixture of two isomers represented by compounds IIIA and IIIB in FIG. 4, which may be employed together or may be separated by one or more techniques for separating positional isomers such as, but not limited to, liquid chromatography (TLC, HPLC, RPLC, HTLC) and gas chromatography, for example.

Figure 5:
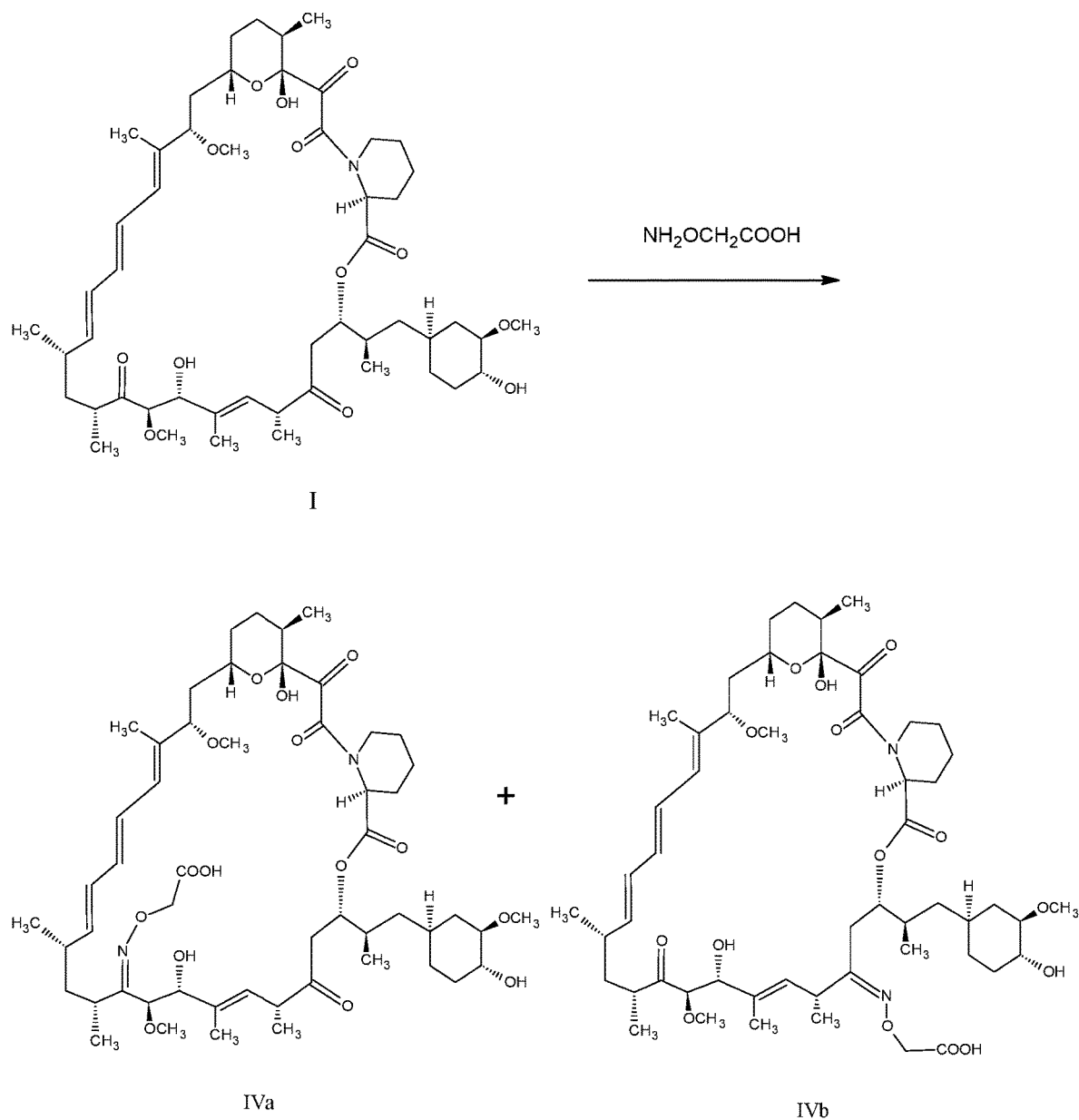
FIG. 5 is a reaction scheme for the preparation of oxime derivatives of sirolimus in another example in accordance with the principles described herein.
Figure 6:
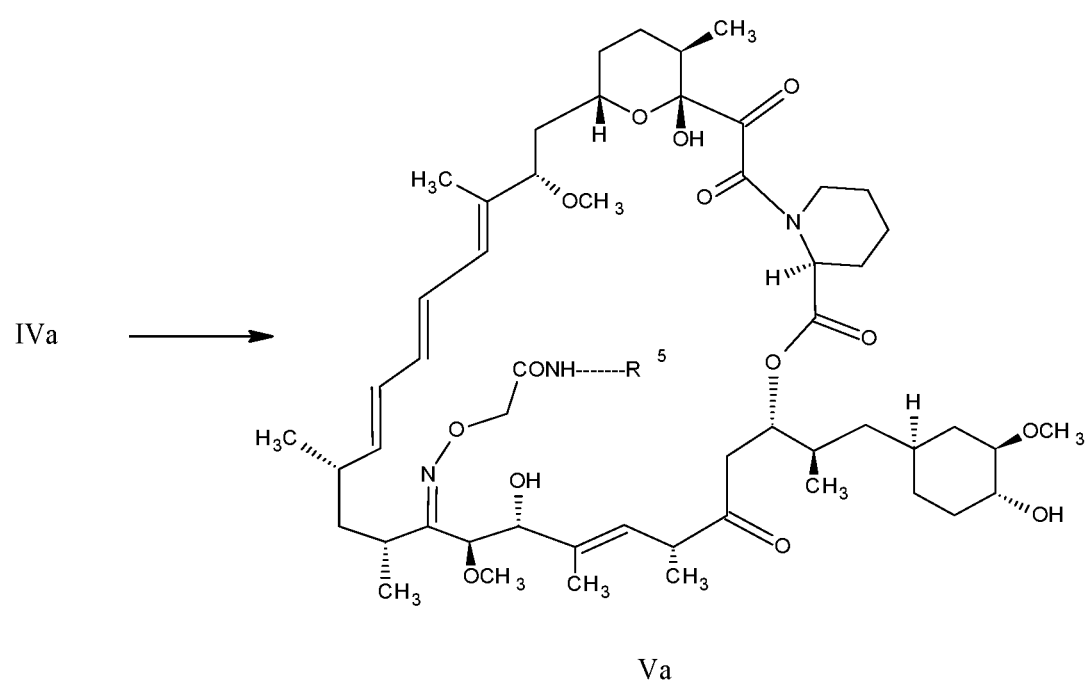
FIG. 6 is a reaction scheme for the preparation of an immunogen from an oxime derivative of sirolimus of FIG. 5 in another example in accordance with the principles described herein.

An example of the preparation of an immunogen in accordance with the principles described herein, by way of illustration and not limitation, is set forth in FIGS. 5 and 6. Referring to FIG. 5, sirolimus (I) is reacted with aminooxyacetic acid to form a mixture of oximes of the Formula IVa (representing formation of an oxime at C-26) and IVb (representing formation of an oxime at C-32). The reaction is carried out in an organic solvent such as, for example, an alcohol (e.g., methanol or ethanol), under conditions for forming an oxime. In some examples the temperature during the reaction is about 10° C. to about 30° C., or about 15° C. to about 25° C. The time period of the reaction is about 1 hour to about 30 hours, or about 2 hours to about 24 hours. Compounds IVa and IVb may be separated or the mixture of compounds IVa and IVb may be employed in the next step of the preparation of an immunogen. Separation of IVa and IVb may be carried out by, but not limited to, chromatography (TLC, HPLC, RPLC, HTLC) and gas chromatography, for example.

FIG. 6 depicts, by way of illustration and not limitation, formation of an immunogen from compound IVa. A poly (amino)acid immunogenic carrier ($R^5$ precursor) is combined with compound of IVa to form a compound of the formula Va. The reaction is carried out in an aqueous buffered medium at a pH of about 5.0 to about 7.0, or about 5.5 to about 6.5, or about 6. An activation agent or coupling for facilitating the reaction of the carboxylic acid functionality of Va with an amine group of the $R^5$ precursor is included in the reaction medium. Such coupling agents include, but are not limited to, 1-ethyl-3-(3-dimethylaminopropyl)-carbodiimide (EDAC), N-hydroxysuccinimide (NHS), or N,N,N',N'-tetramethyl-O—(N-succinimidyl)uronium tetrafluoroborate, or combinations of two or more of the above. The reaction is carried out under conditions for forming an amide. In some examples, the reaction medium is an aqueous medium, which may be solely water or may include from 0.1 to about 40 volume percent of a cosolvent, which may be a polar organic solvent such as for example, an amine (e.g., dimethylformamide (DMF)); an alcohol (e.g., ethanol); or an ether (e.g., furan), for example. In some examples the temperature during the reaction is about 15° C. to about 25° C. The time period of the reaction is about 3 hours to about 24 hours, or about 4 hours to about 20 hours, or about 4 hours to about 10 hours, for example. In some examples, by way of illustration and not limitation, the $R^5$ precursor is a protein such as BSA or KLH, for example. An immunogen may also be prepared from compound IVb in a similar manner to that described above for the preparation of immunogen Va. As mentioned above, a mixture of compounds IVa and IVb may also be used to prepare a mixture of immunogens.

Figure 7:
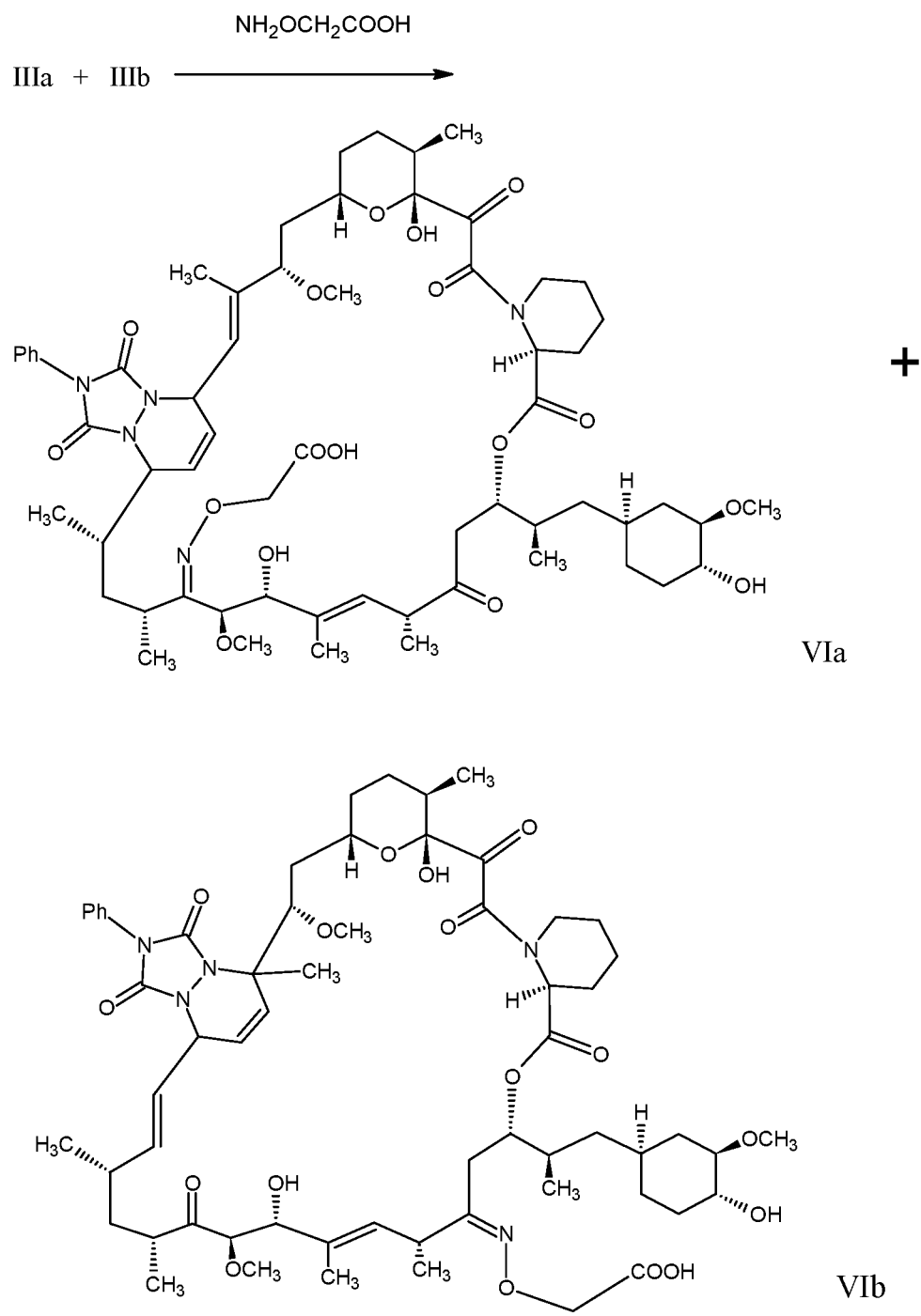
FIG. 7 is a reaction scheme for the preparation of oxime derivatives of sirolimus PTAD adducts of FIG. 4 in another example in accordance with the principles described herein.

FIG. 7 depicts a reaction scheme for the preparation of oximes VIa and VIb from compounds IIIa and IIIb. The reaction is carried out in a manner similar to that described above for FIG. 5. Compound VIa is separated from the mixture of VIa and VIb and is treated (FIG. 8) to prepare immunogens VIIa and VIIb in a manner similar to that described above for the preparation of immunogen Va as discussed above with regard to FIG. 6.

Figure 9:
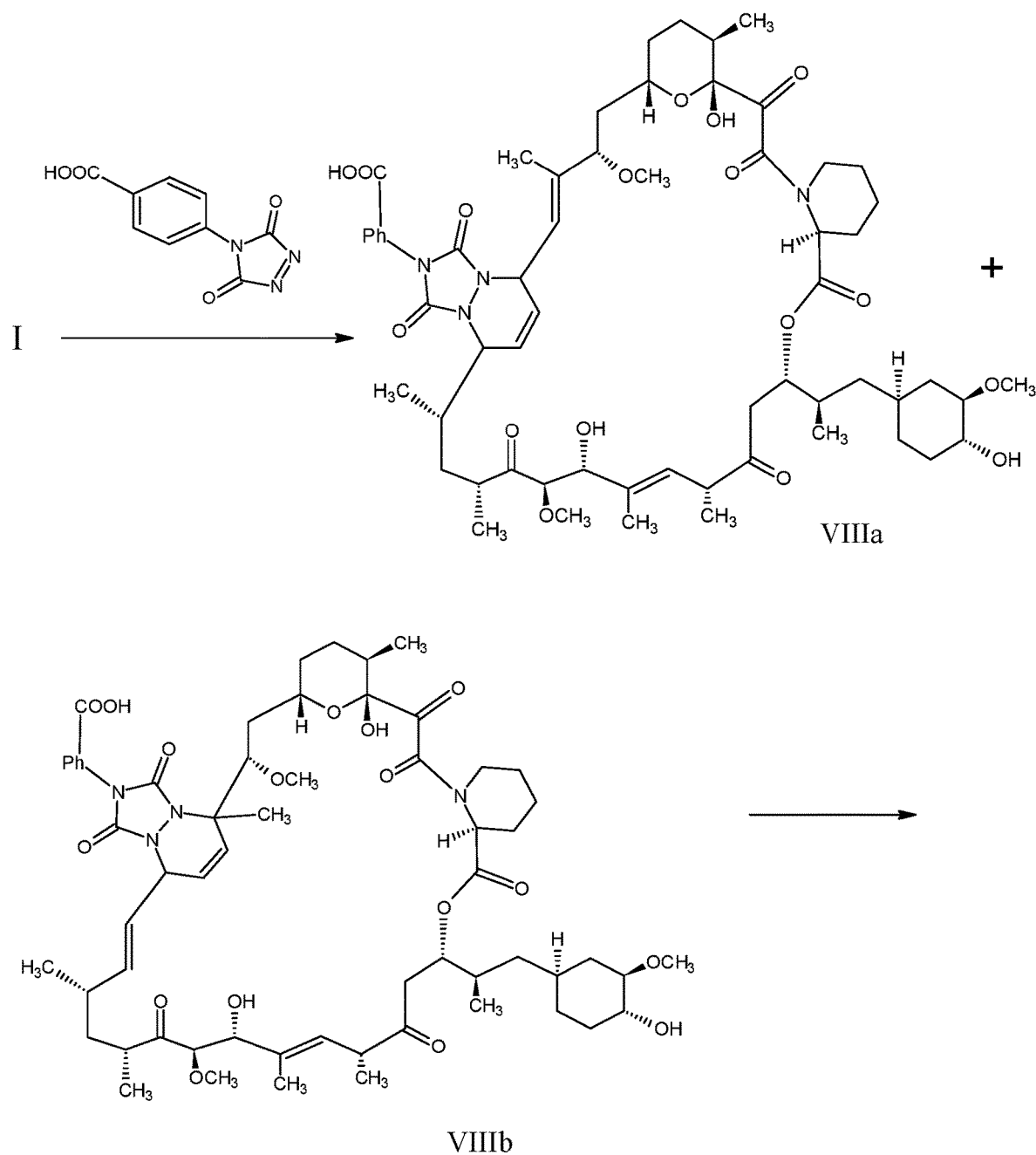
FIG. 9 is a reaction scheme for the preparation of immunogens from an oxime derivative of a carboxylated PTAD adduct of sirolimus in another example in accordance with the principles described herein.
Figure 9:
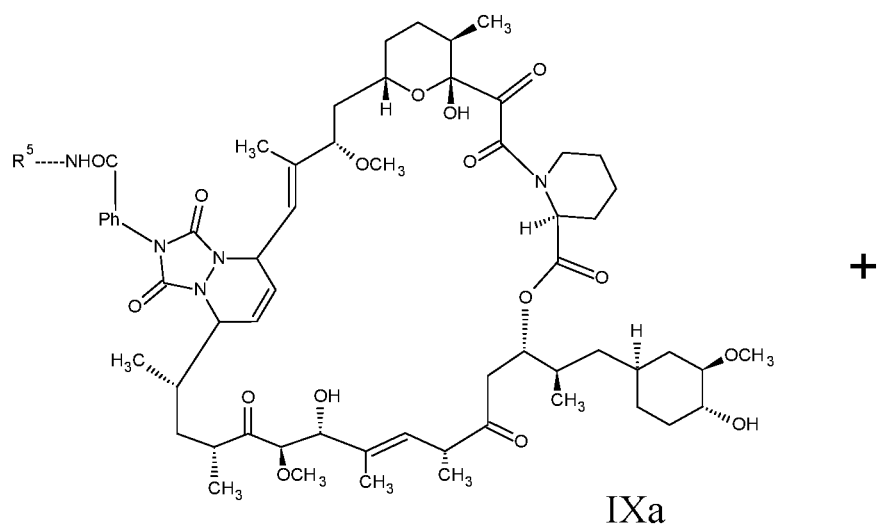
Figure 9:
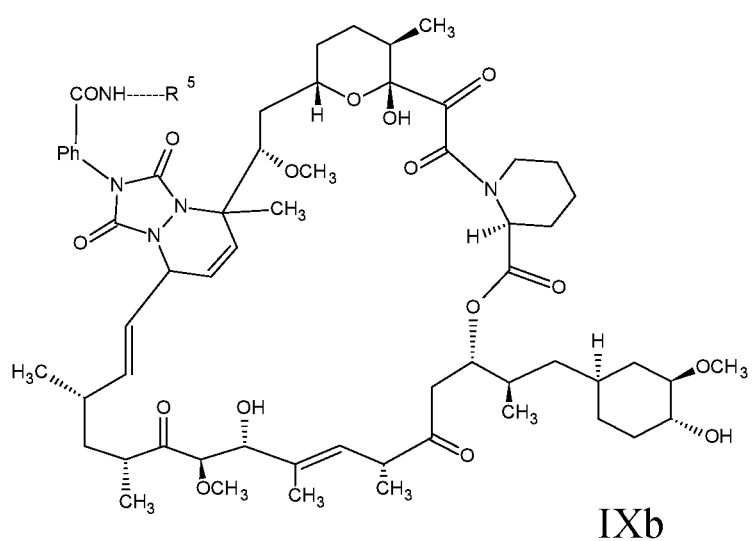

Another example of the preparation of immunogens in accordance with the principles described herein is set forth in FIG. 9. Sirolimus (I) is reacted with a carboxyl derivative of PTAD to give a mixture of compounds VIIIa and VIIIb. The conditions of the reaction are similar to those described above for the preparation of PTAD adducts of sirolimus (I), the details of which are set forth above with reference to FIG. 4. The mixture of compounds VIIIa and VIIIb is treated (FIG. 9) to prepare immunogens IXa and IXb in a manner similar to that described above for the preparation of immunogen Va as discussed above with regard to FIG. 6.

Preparation of Antibodies for Sandwich Assay for Sirolimus

In one example, by way of illustration and not limitation, a first monoclonal antibody is prepared that binds to a portion of sirolimus represented by domain region D1. This first monoclonal antibody may be prepared using compound Va ($R^5$ is BSA), for example, as an immunogen in the methods of antibody production described in detail above. A second monoclonal antibody is prepared that binds to a portion of sirolimus represented by domain region D2. The second monoclonal antibody may be prepared using, for example, compound VIIa or VIIb ($R^5$ is BSA in both) or a mixture of both as an immunogen for antibody preparation in methods described above. Examination of the sirolimus structure by three-dimensional analysis reveals the conformation of regions D1 and D2.

In another example, by way of illustration and not limitation, a first monoclonal antibody is prepared that binds to a portion of sirolimus represented by domain region D1. This first monoclonal antibody may be prepared using compound Va ($R^5$ is KLH), for example, as an immunogen in the methods of antibody production described in detail above. A second monoclonal antibody is prepared that binds to a portion of sirolimus represented by region D3. The second monoclonal antibody may be prepared using, for example, compound IXa or IXb ($R^5$ is KLH in both) or a mixture of both as an immunogen for antibody preparation in methods described above. Examination of the sirolimus structure by three-dimensional analysis reveals the conformation of regions D1 and D3.

General Description of Assays for a Small Molecule

As mentioned above, examples in accordance with the principles described herein enable a sandwich assay for the determination of a small molecule in a sample suspected of containing the small molecule. In the discussion below, an immunosuppressant drug is used as an example, by way of illustration and not limitation, of a small molecule as defined herein. In the sandwich assay, two monoclonal antibodies are employed, each of which bind at the same time to separate regions of the immunosuppressant drug molecule to form an immunocomplex. Detection of the immunocomplex permits the determination of the immunosuppressant drug in the sample.

The sample to be tested is usually a biological sample. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid. In some examples the sample is whole blood, plasma or serum.

Prior to the assay, or in some instances during the assay, the sample may be subjected to one or more pretreatments to lyse cells and/or to release immunosuppressant drug from endogenous binding substances. Lysing cells may be accomplished by use of a hemolytic agent, which is a compound or mixture of compounds that disrupts the integrity of the membranes of red blood cells thereby releasing intracellular contents of the cells. Hemolytic agents include, but are not limited to, non-ionic detergents, anionic detergents, amphoteric detergents, low ionic strength aqueous solutions (hypotonic solutions), bacterial agents, and antibodies that cause complement dependent lysis, for example.

Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis (ethoxylate-block-propoxylate) tetrol, IGEPAL®, MERPOL®, poly(ethylene glycol), 2-[ethyl[(heptadecafluorooctyl)sulfonyl]amino] ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

The nature and amount or concentration of hemolytic agent employed depends on one or more of the nature of the sample, the nature of the immunosuppressant drug, the nature of the rest of the reagent components, and the reaction conditions, for example. The amount of the hemolytic agent is at least sufficient to cause lysis of red blood cells to release contents of the cells. In some examples the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, or about 0.1% to about 0.2%, for example (percent is weight/volume).

The releasing agent is a compound or mixture of compounds that displaces the immunosuppressant drug from endogenous binding moieties. The releasing agent can, and does in many instances, displace metabolites of the immunosuppressant drug from endogenous binding moieties. In many examples the releasing agent has high binding affinity to the endogenous binding proteins so that it readily displaces the immunosuppressant drug, and its metabolites where desired, from endogenous binding proteins. In addition, the releasing agent does not bind to any significant degree to a monoclonal antibody for the drug that is used in an assay. By the phrase "does not bind to any significant degree" is meant that the extent of binding should be low enough so that an accurate assay for the drug may be carried out. The releasing agent, therefore, may be any moiety, either a single compound or a mixture of compounds, which accomplishes the desired result of displacement with no significant binding to an assay antibody.

In some examples the releasing agent is an analog, including structural analogs, of the immunosuppressant drug. An immunosuppressant drug analog is a modified drug that can displace the analogous immunosuppressant drug from a binding protein but does not compete to any substantial degree for a monoclonal antibody for the immunosuppressant drug. The modification provides means to join an immunosuppressant drug analog to another molecule. In an example, the immunosuppressant drug analog may be, for example, the immunosuppressant drug conjugated to another molecule through a linking group. For immunosuppressant drugs that comprise a hydroxy or carboxylic acid functionality, the releasing agent may be an ester of the immunosuppressant drug, which has a high binding affinity for endogenous binding proteins relative to the immunosuppressant drug to be detected and which has no significant binding affinity for an antibody for the immunosuppressant drug. For example, in a determination for tacrolimus, an ester of tacrolimus may be employed as the releasing agent so long as it meets the above requirements. A structural analog is a moiety that has the same or similar structural or spatial characteristics as the immunosuppressant drug such that the structural analog accomplishes the same or similar result as the analog of the immunosuppressant drug. The structural analog may be, for example, another compound that is related to the immunosuppressant drug. For example, in a determination for tacrolimus, an ester of sirolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, $D-Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference.

The concentration of the releasing agent in the medium is that sufficient to achieve the desired result of displacing the immunosuppressant drug, and in some instances the metabolites of the immunosuppressant drug, from endogenous binding moieties to render the drug and metabolites accessible for binding to an antibody for the drug as discussed above. The amount or concentration of the releasing agent employed depends on one or more of the nature of the sample, the nature of the immunosuppressant drug, the nature of the drug metabolites, the nature of other reagent components, and the reaction conditions, for example. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

The assay is an immunoassay, which may be performed either without separation (homogeneous) or with separation (heterogeneous) of any of the assay components or products. The homogeneous or heterogeneous assays are carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, or in the range of about 5 to about 10, or in the range of about 6.5 to about 9.5. The pH will usually be a compromise between optimum binding of the monoclonal antibodies and the immunosuppressant drug, and the pH optimum for other reagents of the assay such as members of the signal producing system, for example.

Various buffers may be used to achieve the desired pH and maintain the pH during the determination. Illustrative buffers include borate, phosphate, carbonate, tris, barbital and the like. The particular buffer employed is not critical to the present disclosure, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; for example.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, such as (but not limited to) room temperature, during the period of the measurement. Incubation temperatures range from about 5° to about 99° C., or about 15° C. to about 70° C., or about 20° C. to about 45° C. The time period for the incubation is about 0.2 seconds to about 6 hours, or about 2 seconds to about 1 hour, or about 1 to about 5 minutes. The time period depends on the temperature of the medium and the rate of binding of the various reagents, which is determined by the association rate constant, the concentration, the binding constant and dissociation rate constant. Temperatures during measurements range from about 10° C. to about 50° C., or from about 15° C. to about 40° C.

The concentration of immunosuppressant drug analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the immunosuppressant drug analyte. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the immunosuppressant analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

In the assays discussed above, one or more labels are employed wherein the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the immunosuppressant drug being detected or to an agent that reflects the amount of the immunosuppressant drug to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, as the case may be.

Suitable labels include, by way of illustration and not limitation, enzymes such as β-galactosidase, alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chrome particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members or one or more of the monoclonal antibodies can be bound to a support. A monoclonal antibody may be bound to a solid support in any manner known in the art, provided only that the binding does not substantially interfere with the ability to bind with a region of the immunosuppressant drug. In some examples, the label or other sps member or the monoclonal antibody may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the moiety to be coupled. The linking group may be one as described above for the linking of immunogen to an immunosuppressant drug molecule. Other methods of binding to a support may also be employed. For instance, a solid support may have a coating of a binder for a small molecule such as, for example, avidin or an antibody, where a small molecule such as, e.g., biotin or a hapten, can be bound to the moiety to be coupled or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, and DENDRIMERS, for example. Depending on the type of assay, the support may or may not be suspendable in the medium in which it is employed. Examples, by way of illustration and not limitation, of suspendable supports are polymeric materials such as latex, lipid bilayers or liposomes, oil droplets, cells and hydrogels, and magnetic particles, for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), for example; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, such as (but not by way of limitation) of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus,* and *E. coli,* viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chrome particles or latex particles.

The polymer particles can be formed of addition or condensation polymers. The particles will be readily dispersible in an aqueous medium and can be adsorptive or functionalizable so as to permit conjugation to a monoclonal antibody for an immunosuppressant drug, either directly or indirectly through a linking group. The linking group may be one as described above for the linking of immunogens to an immunosuppressant drug molecule. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to one or both of the two different monoclonal antibodies. Bonding of the label to the sbp member may be accomplished by chemical reactions that result in replacing a hydrogen atom of the label with a bond to the monoclonal antibody or may include a linking group between the label and the monoclonal antibody. The linking group may be one as described above for the linking of immunogens to an immunosuppressant drug molecule. Other sps members may also be bound covalently to the monoclonal antibodies. For example, two sps members such as a fluorescer and quencher can each be bound, respectively, to the monoclonal antibodies where the fluorescer is bound to one of the monoclonal antibodies and a quencher is bound to the other of the monoclonal antibodies. When the two different monoclonal antibodies bind to the immunosuppressant drug, the formation of a sandwich complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include, but are not limited to, saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, such as (but not limited to) hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems addition of a substrate and/or a cofactor may be necessary.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the sirolimus compound present in a sample. Temperatures during measurements may range from about 10° to about 70° C., or from about 20° to about 45° C., or from about 20° to about 25° C. In one approach standard curves are formed using known concentrations of the analytes to be screened. As discussed above, calibrators and other controls may also be used.

The phrase "measuring the amount of an immunosuppressant drug" refers to the quantitative, semi-quantitative and qualitative determination of the immunosuppressant drug. Methods that are quantitative, semi-quantitative and qualitative, as well as all other methods for determining the immunosuppressant drug, are considered to be methods of measuring the amount of the immunosuppressant drug. For example, a method, which merely detects the presence or absence of the immunosuppressant drug in a sample suspected of containing the immunosuppressant drug, is considered to be included within the scope of the present disclosure. The terms "detecting" and "determining," as well as other common synonyms for measuring, are contemplated within the scope of the present disclosure.

In one example in accordance with the principles described herein, one of the monoclonal antibodies specific for a region of an immunosuppressant drug is bound to a support and the other of the monoclonal antibodies that is specific for a region of the immunosuppressant drug that is spatially separated from the region of the immunosuppressant drug to which the other monoclonal antibodies binds is bound to an sps member such as, for example, a label. The sample suspected of containing the immunosuppressant drug is combined in a suitable medium with the two conjugated monoclonal antibodies and the medium is incubated. Then, the medium is examined for the one or both of the presence and amount of an immunocomplex formed by the two different monoclonal antibodies and the immunosuppressant drug from the sample. The support may or may not be separated from the medium prior to the examination. The presence and/or amount of the immunocomplex is determined by determining the presence and/or amount of the label in the medium or on the support.

In one particular example, a capture assay is employed. In this assay format, one monoclonal antibody is covalently bound to a magnetic particle such as, for example, a chrome (chromium dioxide) particle. The sample is incubated with these particles to allow the immunosuppressant drug in the sample to bind to the monoclonal antibody on the magnetic particle. Subsequently, a second monoclonal antibody conjugated to an enzyme such as, for example, β-galactosidase, is incubated with the magnetic particles. After application of a magnet and washing of the magnetic particles, the amount of enzyme that is bound to the magnetic particles is measured and is directly related to the presence and/or amount of the immunosuppressant drug in the sample. In this approach substrate of the reporter enzyme is added to the final reaction container, and the enzyme activity is measured spectrophotometrically as a change in absorbance overtime.

In an alternative approach, the magnetic particle reagent is added in an excess amount, i.e., an amount greater than that required to bind all of the immunosuppressant drug that might be present in the sample. Then, a magnet is applied to separate the magnetic particles from the medium and the magnetic particles are washed and resuspended in assay medium. The enzyme conjugated to the second monoclonal antibody is added and the medium is incubated followed by signal determination as described above.

In another example, by way of illustration and not limitation, chemiluminescent particles are employed, which comprise the chemiluminescent compound associated therewith such as by incorporation therein or attachment thereto. One of the monoclonal antibodies for the immunosuppressant drug is bound to the particles such as through the intermediacy of a polysaccharide coating the particles. The other monoclonal antibody that binds to the immunosuppressant drug is part of a biotin conjugate. Streptavidin is conjugated to a second set of particles having a photosensitizer associated therewith. The chemiluminescent particles are mixed with a sample suspected of containing the immunosuppressant drug and the photosensitizer particles. The reaction medium is incubated to allow the particles to bind to the immunosuppressant drug by virtue of the binding of the monoclonal antibodies to the immunosuppressant drug. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the immunosuppressant drug, it is activated by singlet oxygen and emits luminescence. The medium is then examined for the presence and/or the amount of luminescence or light emitted, the presence thereof being related to the presence and/or amount of the immunosuppressant drug in a sample.

Kits for Conducting Assays

The reagents for conducting a particular assay may be present in a kit useful for conveniently performing an assay for the determination of a small molecule such as, for example, an immunosuppressant drug analyte. In one example, a kit comprises in packaged combination reagents for analyzing for the analyte, the nature of which depend upon the particular assay format. The reagents may include, for example, one or more monoclonal antibodies in accordance with the principles described herein, which may be conjugated to a label or a support. The reagents may each be in separate containers or various reagents can be combined in one or more containers depending on the cross-reactivity and stability of the reagents. The kit can further include other separately packaged reagents for conducting an assay such as additional binding members and ancillary reagents.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designation "first" and "second" is completely arbitrary and is not meant to suggest any order or ranking among any members of a group to which the above language pertains such as, for example, "first and second monoclonal antibodies" or "first monoclonal antibody" and "second monoclonal antibody."

The following examples further describe the specific embodiments of the present disclosure by way of illustration and not limitation and are intended to describe and not to limit the scope of the present disclosure. Parts and percentages disclosed herein are by volume unless otherwise indicated.

EXAMPLES

All chemicals were purchased from the Sigma-Aldrich Company (St. Louis Mo.) unless otherwise noted.

Testing was carried out using the DIMENSION® RxL analyzer, available from Siemens AG, Newark Del. The instrument was employed using enzymatic detection system with sandwich immunoassay format. In the embodiment of the sandwich method used herein and discussed in more detail below, binding between a labeled antibody (Ab) conjugated to an enzyme (conjugate) and sirolimus drug (SIRO) in patient samples and subsequent binding of the resulting immunocomplex with a capture antibody on chrome particles determined the amount of sirolimus in the patient samples. The unbound tag antibody enzyme conjugate was removed automatically by 3-4 mix/wash and magnetic separation cycles. The enzymatic activity from conjugate remaining on the chrome particles was measured and was directly proportional to the amount of sirolimus in the patient sample.

Definitions mg=milligram
g=gram(s)
ng=nanogram(s)
mL=milliliter(s)
µL=microliter(s)
mmol(s)=millimole(s)
µmol=micromolar
° C.=degrees Centigrade
min=minute(s)
sec=second(s)
hr=hour(s)
w/v=weight to volume
v/v=volume to volume
TLC=thin layer chromatography
HPLC=high performance liquid chromatography
UV=ultraviolet
EtOAc=ethyl acetate
MeOH=methanol
DMF=dimethylformamide
DI=deionized
THF=tetrahydrofuran
NHS=N-hydroxysuccinimide
DCC=N,N-dicyclohexyl carbodiimide
BSA=bovine serum albumin
BGG=bovine gamma globulin
MS=mass spectrometry
SIRO=sirolimus
rotovap=rotary evaporator

Example 1

Preparation of Compounds

Preparation of C-32-Sirolimus and C-26-Sirolimus Oximes (IVa and IVb) (FIG. 5). To a solution of Sirolimus (I) (653.6 mg, 0.715 mmol) and carboxymethoxyamine hemihydrochloride (234.4 mg, 2.14 mmol) in MeOH (20 mL) was added sodium acetate (181.8 mg, 3.1 mmol). The reaction mixture was stirred at room temperature (23° C.) overnight (18 hr) under a nitrogen atmosphere. TLC analysis indicated that the reaction was completed. (TLC, Silica gel plate, $CH_2Cl_2$/MeOH=9/1). $CH_2Cl_2$ (80 mL) and DI water (20 mL) was added to the mixture, which was stirred 10 min. The $CH_2Cl_2$ layer was separated. The aqueous layer was extracted with $CH_2Cl_2$ (3×30 mL). The combined $CH_2Cl_2$ solutions were washed with DI water (2×40 mL), were dried over Na2SO4, were filtered and were concentrated on a rotovap to give a mixture of C-32-Sirolimus and C-26-Sirolimus oximes (IVa and IVb, 622 mg).

Isolation of C-26-Sirolimus Oxime (IVa) (FIG. 5). An optimal TLC condition (silica gel, EtOAc/Hexanes/MeOH=5/2/1, $R_f$ C-32-oxime=0.59, $R_f$ C-26-oxime=0.51) for the separation of C-32-Sirolimus and C-26-Sirolimus oximes was developed and applied successfully in an BIOTAGE® ISOLERA™ One Flash Chromatography System (John Morris Scientific, Chatswood, NSW). A mixture of C-32-Sirolimus and C-26-Sirolimus oximes (IVa and IVb, 622 mg) was dissolved in $CH_2Cl_2$ (5 mL). The $CH_2Cl_2$ solution was eluted to a cartridge (silica, 50 g SNAP Ultra) associated with the BIOTAGE® ISOLERA™ One Flash Chromatography System. The system was run with mixed solvent in a flow rate of 25 mL/min. All the collected fractions from the cartridge were checked by TLC (EtOAc/Hexanes/MeOH=5/2/1). Base on TLC analysis, the more polar pure fractions ($R_f$ C-26-oxime=0.51) were combined and concentrated to give C-26-Sirolimus oximes (IVa) (197 mg). HPLC-UV analysis of this compound indicated a purity of 95%.

Preparation of C-26-Sirolimus Oxime-BSA Conjugate (Va) ($R^5$=BSA in FIG. 6). To a solution of IVa (167.97 mg, 0.17 mmol) in THF/DMF (8 mL THF, 0.4 mL DMF), NHS (41.8 mg, 0.35 mmol) and DCC (70.9 mg, 0.34 mmol) was added. The reaction mixture was stirred at room temperature under a nitrogen atmosphere and the product NHS ester is slightly less polar than compound IVa in TLC analysis. A white solid formed during the reaction was filtered and then washed with EtOAc. After solvent was removed, the reaction mixture was re-dissolved in EtOAc and filtered; evaporation of solvent afforded a slight yellow solid, which was held under high vacuum for 1 hr.

The activated hapten NHS ester (slight yellow solid) was dissolved in DMF (1 mL) and the solution was added dropwise to a BSA (120 mg) in phosphate buffered saline (PBS) buffer (0.1 M $NaH_2PO_4$/$Na_2HPO_4$, pH 8) (14 mL) in an ice bath. After stirring for 1 hr at room temperature, pH of the solution was adjusted to pH 8 with NaOH (1N) and the mixture was stirred in a cold room (4° C.) overnight. The BSA conjugate was purified through an equilibrated SEPHADEX® G-25 column (C26×70) with PBS buffer (0.1 M $NaH_2PO_4$/$Na_2PO_4$, pH 7), and eluted with same PBS buffer. A UV detector at 280 nm was used to monitor the eluted fractions from the column. A clean separation between BSA conjugate and the unconjugated hapten IVa was observed. Fractions containing BSA conjugate (Va) were pooled to a total of 57 mL, and the concentration of the Va was determined to be 2.52 mg/mL by the BCA Protein Concentration Assay (Pierce Biotechnology, Rockford Ill.).

Preparation of Diels-Alder adduct of 4-phenyl-1,2,4-triazoline-3,5-dione (PTAD) and sirolimus (I). Reference is made to FIG. 4. A solution of PTAD (38 mg, 0.217 mmols) in anhydrous $CH_2Cl_2$ (1 ml) was added to a solution of sirolimus (I) (200 mg, 0.219 mmols) in anhydrous $CH_2Cl_2$ (7 ml) at room temperature (24° C.). The characteristic red color of PTAD disappeared. The reaction mixture was stirred at room temperature for 30 minutes and refluxed under nitrogen at 60° C. for 60 min. TLC analysis of the mixture showed that very small amount of sirolimus remained. (TLC conditions: Hexane/ethyl acetate/MeOH=30/65/5 (v/v)). Then, 5 mg of PTAD was added to the reaction mixture. The mixture was stirred at 24° C. for 30 min. TLC analysis of the mixture again demonstrated that all sirolimus was consumed. The light red color of PTAD remained in the reaction indicating an excess of PTAD. Most of the $CH_2Cl_2$ was evaporated by rotary evaporation. The residue solution (0.5 ml) was applied to a preparative TLC plate (20×20 cm, 2000 micron; Analtech, Newark Del.). The plate was developed with the same solvent system as above (Hexane/ethyl acetate/MeOH=30/65/5 (v/v)). The silicon band containing product was collected and extracted with MeOH/$CH_2Cl_2$ (1/9; v/v; 40 ml×3) three times. The combined organic extracts were evaporated and the residue was dried in high vacuum for 16 hr. This gave a mixture of the desired pure PTAD-sirolimus Diels-Alder adducts IIIa and IIIb (220 mg, 92% yield) as a white solid. HPLC regionisomers ratio of IIIa/IIIb was 86/14; HPLC-MS (ES): MNa+ 1111.5; 1H-NMR (CDCl$_3$) 7.62 (1H); 7.46 (3H); 7.37 (1H); 5.98 (1H); 5.84 (1H); 5.55 (1H); 3.4 (s, 3H); 3.35 (s, 3H); 3.15 (s, 3H); 0.72 (q, 1H).

Preparation of Oximes of Compounds IIIa and IIIb (FIG. 7). Oximes VIa and VIb are prepared from Compounds IIIa and IIIb in a manner similar to that described above for the Preparation of C-32-Sirolimus and C-26-Sirolimus Oximes (IVa and IVb) of FIG. 5.

Figure 8:
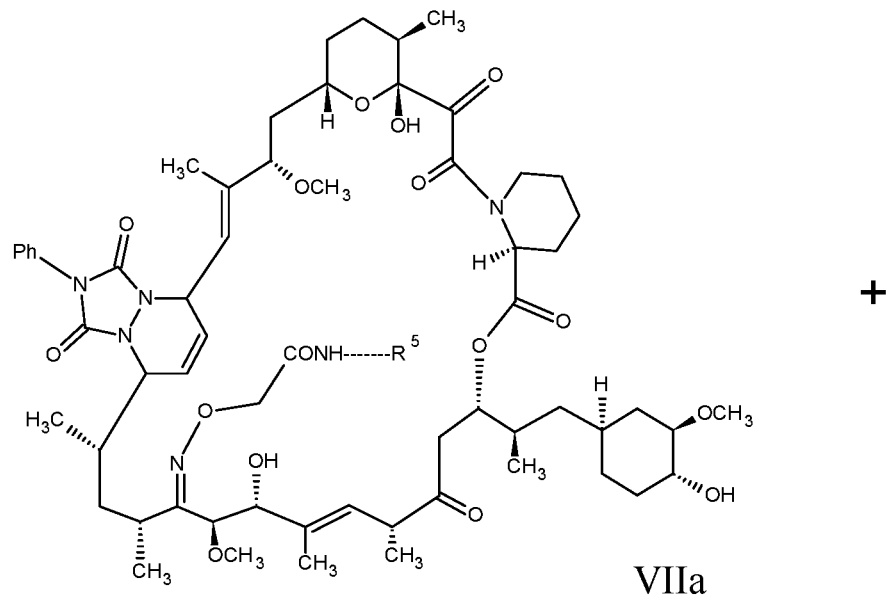
FIG. 8 is a reaction scheme for the preparation of an immunogen from an oxime derivative of sirolimus of FIG. 7 in another example in accordance with the principles described herein.
Figure 8:
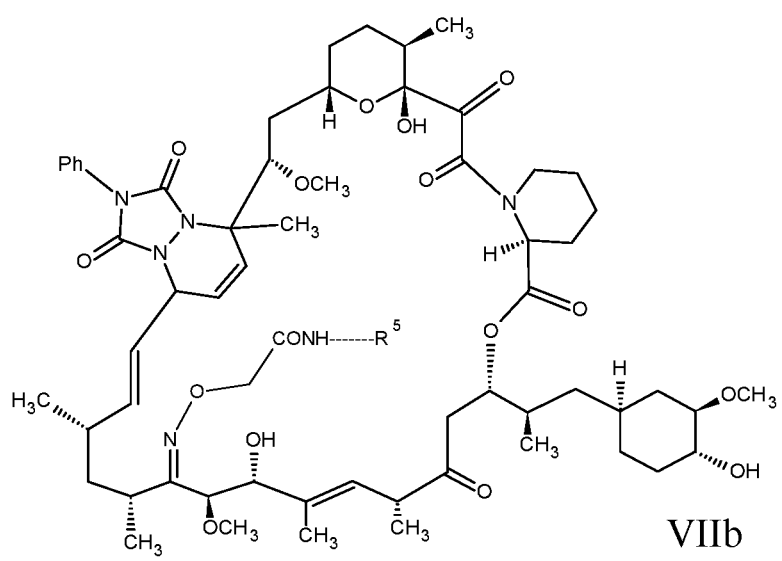

Preparation of BSA Conjugates (VIIa and VIIb) ($R^5$=BSA in FIG. 8). Oxime VIa is isolated from the above mixture of VIa and VIb in a manner similar to that described above for the isolation of IVa of FIG. 5. BSA conjugates VIIa and VIIb are prepared from VIa in a manner similar to that described above for the preparation of BSA conjugate Va.

Preparation of KLH Conjugates (VIIa and VIIb) ($R^5$=KLH in FIG. 8). Oxime VIa is isolated from the above mixture of VIa and VIb in a manner similar to that described above for the isolation of IVa of FIG. 5. KLH conjugates VIIa and VIIb are prepared from VIa in a manner similar to that described above for the preparation of BSA conjugate Va.

Preparation of Monoclonal Antibody that Binds to Domain D3 of Sirolimus. Monoclonal antibodies that bind to separate portions of the sirolimus molecule are prepared as follows. The immunogen is KLH conjugates VIa and VIb prepared as described above. This immunogen is used to immunize Balb/c mice. The first immunization is 25 µg in a volume of 200 µl with monophosphoryl lipid A and synthetic trehalose dicorynomycolate adjuvant (RIBI MPL+TDM Emulsion, RIBI ImmunoChem Research Inc., Hamilton Mont.) intraperitoneally. Five weeks later a boost immunization is given with 25 µg of the immunogen in 200 µl of monophosphoryl lipid A and synthetic trehalose dicorynomycolate adjuvant intraperitoneally. Subsequently, after another 8 weeks, a prefusion boost is given of the 25 µg of the immunogen in 200 µl of Hanks' Balanced Salt Solution intravenously and intraperitoneally.

Three days later, fusion is performed by standard methods using a nonsecreting murine myeloma designated P3x63-AG8.653. Cloning is carried out by standard methods.

The clones are screened by the following reverse ELISA immunoassay procedure according to the following protocol. Plates are coated with polyclonal goat anti-mouse IgG (IgG+IgA+IgM) (Zymed Laboratories, South San Francisco Calif.) at 5 µg/ml in phosphate buffered saline at 100 µl per well. Plate coating is performed for 2 hours or more at room temperature or overnight at about 4° C. The plates are then flicked dry and blocked with 300 µl per well of blocking buffer diluent (0.5% bovine serum albumin, 0.05% TWEEN® 20 in PBS). Plate blocking is performed by incubation for 15 minutes or more at room temperature with plate shaking. The plates are then flicked dry. The monoclonal antibody to be screened is then added to each well as follows: 50 µl per well of blocking buffer diluent was added along with 50 µl per well culture supernatant transferred from the corresponding well in the fusion growth plate. Incubation is for about 1 hour at room temperature with shaking. The plate is washed using a TITERTECK PLUS® plate washer with S20 stacker with the washing buffer being PBS with 0.05% TWEEN® 20. An enzyme conjugate of sirolimus covalently coupled to glucose-6-phosphate dehydrogenase diluted in blocking buffer diluent to 1:4000 is added at 100 µl per well. Incubation is performed for about 1 hour at room temperature with shaking. The plate is then washed and a chromogenic solution is added at a volume of 100 µl per well. The chromogenic solution contains 0.593 mM p-iodonitrotetrazolium violet, 0.02 M NAD, 0.033 M glucose-6-phosphate, 0.055 M Tris, 0.02% sodium azide, and a 1:4000 dilution of diaphorase (lipoyl dehydrogenase). BSA is present at 1% (vol/vol) of a 5% w/vol BSA solution. BSA is used to help prevent rapid precipitation of reduced p-iodonitrotetrazolium violet.

From the screening a hybridoma producing a suitable monoclonal antibody that binds to domain D3 of sirolimus is selected.

Preparation of hemolytic pretreatment solution. This pretreatment solution contains 5 µg/mL of FK506, 6.8 mg/mL PIPES™ 1.5 sodium salt, 0.3 mg/mL EDTA Disodium, 1.0 mg/mL Saponin, 0.2% PROCLIN® 300, 0.024 mg/mL Neomycin sulfate and 0.99 mg/mL NaN3, pH 6.5. The FK506 concentration in the final reaction mixture is 1.1 µg/mL.

Example 2

Determination of Sirolimus Using Automated Chrome Particle Sandwich Assay

Preparation of anti-sirolimus F(ab')$_2$-β-galactosidase conjugate using a monoclonal antibody that binds to domain D3 of sirolimus. Monoclonal anti-sirolimus antibody that binds to domain D3 of sirolimus (prepared as described above in Example 1) is fragmented to F(ab')$_2$ using lysyl-endopeptidase (Wako, Richmond, Va.) digestion and then is conjugated to β-galactosidase using a standard heterobifunctional SMCC (succinimidyl trans-4-(N-maleimidylmethyl)cyclohexane-1-carboxylate) linker according to known techniques. The antibody conjugate solution contains approximately 2.0 µg/mL anti-sirolimus antibody-β-galactosidase conjugate, 30 mg/mL protease free bovine serum albumin, 0.126 mg/mL MgCl$_2$, 0.03 mL/mL of ethylene glycol, 24.5 mg/mL HEPES, 38.5 mg/mL Na HEPES, 50 mg/mL NaCl and beta-gal mutein (inactivated beta-galactosidase), pH 7.8.

Magnetic chrome particle preparation. Chrome particles (immunoassay solid phase) are prepared by conjugating a monoclonal antibody that binds to domain D1 of sirolimus (prepared as described above in Example 1 using as an immunogen C-26-Sirolimus Oxime-BSA Conjugate (Va) ($R^5$=BSA in FIG. 6)) to glutaraldehyde coated chromium dioxide particles. The chrome reagent contains chrome particles and 60.4 mg/mL trehalose dihydrate and 7.2 mg/mL polyethylene glycol (PEG) 8000. Three chrome particle concentrations, namely 5, 2.5, and 1.67 mg/mL, are used in the study.

Sandwich sirolimus Assay. The principle and operation of the Sandwich assay for sirolimus is as follows: A whole blood sample (50 µL) containing sirolimus is combined with a hemolytic pretreatment reagent prepared as described above in a reaction vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood and the displacement of the protein-bound sirolimus molecules from their binding domains.

Anti-sirolimus F(ab')$_2$-β-galactosidase conjugate prepared using the monoclonal antibody that binds to the D3 domain of sirolimus (50 µL) is added to the reaction vessels and the mixture is held for a period of time (35 sec) and at a temperature of 43° C. to allow sirolimus, if present, to react with the antibody enzyme conjugate. Chrome particles with immobilized monoclonal antibody that binds to domain D1 of sirolimus are added (50 µL) to the reaction vessels and are allowed to bind the anti-sirolimus F(ab')$_2$-β-galactosidase complex to form a sandwich. This reaction mixture is incubated for 14 min at a temperature of 43° C. before the automated magnetic separation, mix and wash cycles begin on the DIMENSION® instrument. A total of 4 separation/wash cycles are employed to remove the unbound anti-sirolimus F(ab')$_2$-β-galactosidase conjugate and debris from sample. The automated chrome washes are conducted on board using Chemistry Wash solution at pH 8.0 in HEPES buffer, both of which were provided for the DIMENSION® Heterogeneous Immunoassay Module. The washed chrome particles are then re-suspended in the Chemistry Wash solution by ultrasound mixing and a portion (54 µL) of the suspended chrome particles are transferred to a photometric cuvette to mix with a β-galactosidase substrate solution (chlorophenol red-β-D-galactopyranoside, or CPRG). The sirolimus bound to the anti-sirolimus F(ab')$_2$-β-galactosidase conjugate on the chrome particle surface is detected by measuring the enzymatic rate of the conjugate in the presence of CPRG. The rate for each reaction vessel is measured bichromatically at 577 and 700 nm. The results indicate successful detection of sirolimus.

Example 3

Determination of Sirolimus Using Automated ELISA Sandwich Assay

Sandwich enzyme-linked immunosorbent assay (ELISA) for sirolimus. The following steps are employed: Step 1: 50 µL of purified monoclonal antibody that binds to domain D1 of sirolimus (prepared as described above in Example 1 using as an immunogen C-26-Sirolimus Oxime-BSA Conjugate (Va) ($R^5$=BSA in FIG. 6)) (10 µg/mL in PBS) is coated on ELISA plates overnight at 4° C. Plates are washed using MILLI-Q® water (Millipore Corporation, Billerica Mass.) containing 0.05% TWEEN® 20. Step 2: 200 µL of PCT Blocker solution (0.5% Casein (milk protein) in phosphate buffer containing 0.05% TWEEN® 20) is added to each well and the media are incubated at room temp for 30 min. Plates are washed using MILLI-Q® water containing 0.05% TWEEN® 20. Step 3: 50 μL of desired concentration of sirolimus diluted in PBS is added to the respective wells and the media are incubated at room temperature for 30 min. Plates are washed using MILLI-Q® water containing 0.05% TWEEN® 20. Sirolimus drug concentrations tested are 0, 0.01, 0.02, 0.04, 0.08, 0.16, 0.31, 0.63, 1.25, 2.50, 5.0 and 10.0 ng/mL, respectively. Step 4: The anti-sirolimus F(ab')$_2$-β-galactosidase conjugate prepared using the monoclonal antibody that binds to the D3 domain of sirolimus (prepared in a manner similar to that described above) (1:300 diluted in PCT Blocker solution) is added and the media are incubated at room temperature for 30 min. Plates are washed using MILLI-Q® water containing 0.05% TWEEN® 20. Step 5: β-galactosidase substrate solution (chlorophenol red-β-D-galactopyranoside, or CPRG) is added to each well (100 μL/well). Step 6: The wells are read in plate reader at 577 nm every minute for 20 min. The results indicate successful detection of sirolimus.

All publications and patent applications cited in this specification are herein incorporated by reference as if each individual publication or patent application were specifically and individually indicated to be incorporated by reference.

Although the foregoing has been described in some detail byway of illustration and example for purposes of clarity of understanding, it will be readily apparent to those of ordinary skill in the art in light of the teachings of the present disclosure that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present disclosure are presented for purposes of illustration and description; they are not intended to be exhaustive or to limit the invention to the precise forms disclosed. Many modifications and variations are possible in view of the above teachings. The embodiments were chosen and described in order to explain the principles of the present disclosure and its practical applications and to thereby enable others skilled in the art to utilize the invention.

What is claimed is:

1. A method of designing monoclonal antibodies for a sandwich assay for sirolimus, wherein sirolimus has spatially separate binding portions such that two different antibodies can bind simultaneously to the same sirolimus molecule without interfering with the binding of each other to form a three-member complex, the method comprising:

immunizing a first antibody-producing animal with a first immunogen comprising sirolimus linked at carbon atom 26 and/or 32 through an oxime functionality to an immunogenic carrier, wherein the immunogenic carrier of the first immunogen is selected from the group consisting of bovine serum albumin (BSA), keyhole limpet hemocyanin (KLH), egg ovalbumin, bovine gamma globulin (BGG), thyroglobulin, ovalbumin, fibrinogen, and a polysaccharide;

isolating antibody-producing spleen cells from the first antibody-producing animal;

selecting at least one antibody-producing spleen cell that secretes a first monoclonal antibody;

preparing a first hybrid cell line by fusing the selected antibody-producing spleen cell(s) from the first antibody-producing animal with an appropriate fusion partner, whereby the first hybrid cell line secretes the first monoclonal antibody;

immunizing a second antibody-producing animal with a second immunogen comprising a modified sirolimus of at least one of formula IIA and IIB, and wherein the modified sirolimus is further linked to an immunogenic carrier at ring atom 26 and/or ring atom 32 for eliciting antibodies, and wherein the immunogenic carrier of the second immunogen is selected from the group consisting of bovine serum albumin (BSA), keyhole limpet hemocyanin (KLH), egg ovalbumin, bovine gamma globulin (BGG), thyroglobulin, ovalbumin, fibrinogen, and a polysaccharide;

wherein IIA and IIB are compounds of the formulas:

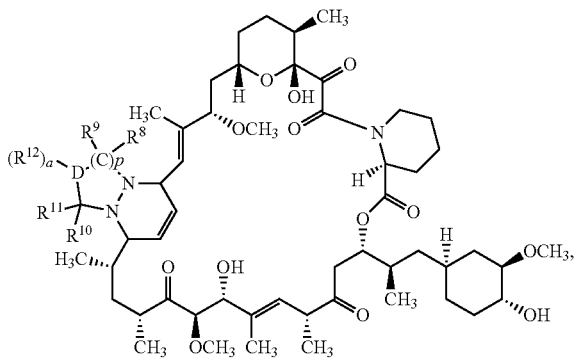

IIA

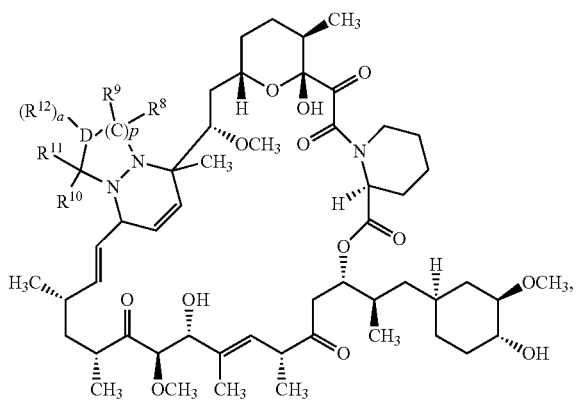

IIB wherein:

$R^8$ and $R^9$ are taken together to form a double bond to O, and p is 1;

$R^{10}$ and $R^{11}$ are taken together to form a double bond to O;

$R^{12}$ is a phenyl group, and a is 1; and

D is N;

isolating antibody-producing spleen cells from the second antibody-producing animal;

selecting at least one antibody-producing spleen cell that secretes a second monoclonal antibody that binds specifically to sirolimus in a portion other than the domain to which the first monoclonal antibody binds; and preparing a second hybrid cell line by fusing the selected antibody-producing spleen cell(s) from the second antibody-producing animal with an appropriate fusion partner, whereby the second hybrid cell line secretes the second monoclonal antibody.

2. The method of claim 1, wherein the step of selecting at least one antibody-producing spleen cell that secretes a first monoclonal antibody is further defined as selecting at least one antibody-producing spleen cell that secretes a first monoclonal antibody that binds specifically to a binding domain extending approximately from ring atom 15 to ring atom 21.

3. The method of claim 1, wherein the first immunogen comprises sirolimus linked at carbon atom 26 through the oxime functionality to the immunogenic carrier.

4. The method of claim 1, wherein the first immunogen comprises sirolimus linked at carbon atom 32 through the oxime functionality to the immunogenic carrier.

5. The method of claim 1, wherein the first immunogen comprises a mixture of sirolimus linked at carbon atom 26 through the oxime functionality to the immunogenic carrier and sirolimus linked at carbon atom 32 through the oxime functionality to the immunogenic carrier.

6. The method of claim 1, wherein the immunogenic carrier of at least one of the first and second immunogens is BSA.

7. The method of claim 1, wherein the immunogenic carrier of at least one of the first and second immunogens is KLH.

8. The method of claim 1, wherein the second immunogen comprises modified sirolimus linked at carbon atom 26 through an oxime functionality to an immunogenic carrier.

9. The method of claim 1, wherein the second immunogen comprises modified sirolimus linked at carbon atom 32 through the oxime functionality to the immunogenic carrier.

10. The method of claim 1, wherein the second immunogen comprises a mixture of modified sirolimus linked at carbon atom 26 through the oxime functionality to the immunogenic carrier and modified sirolimus linked at carbon atom 32 through the oxime functionality to the immunogenic carrier.

11. The method of claim 1, wherein the first immunogen comprises formula Va:

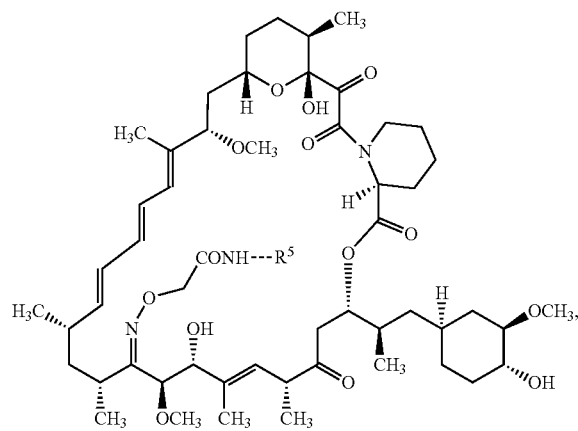

Va wherein $R^5$ is BSA or KLH.

12. The method of claim 1, wherein the second immunogen comprises a modified sirolimus of at least one of formula IIIa and IIIb:

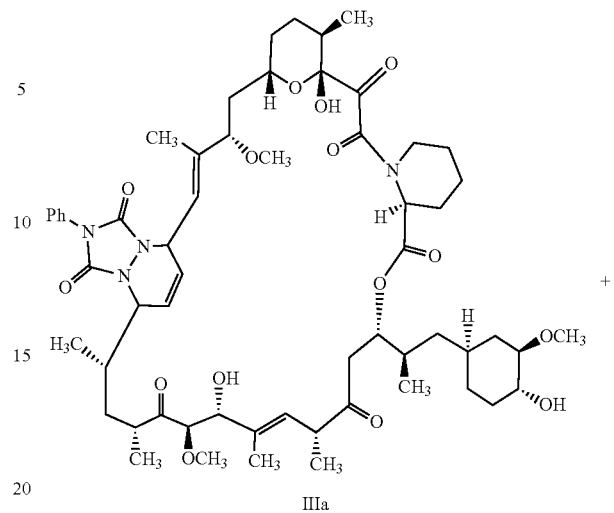

IIIa

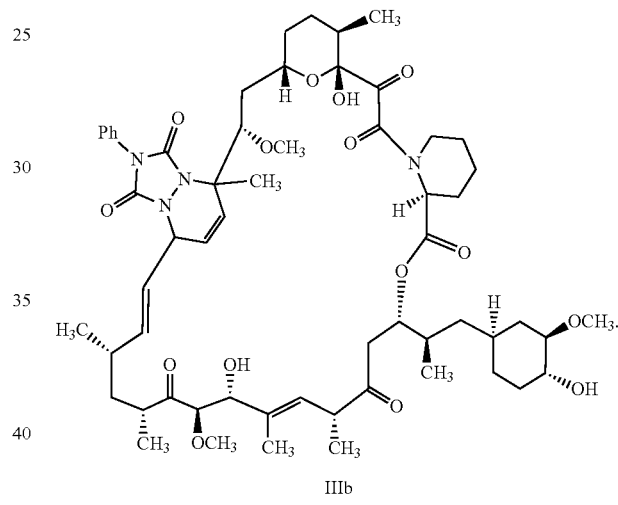

IIIb

13. The method of claim 1, wherein the second immunogen is at least one of formula VIIa and VIIb:

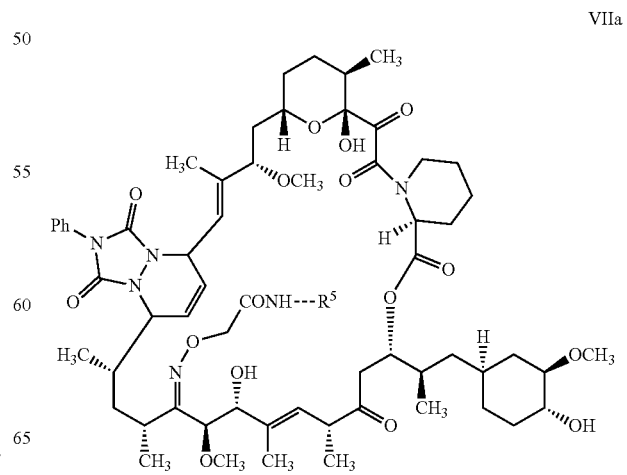

VIIa

-continued
VIIb
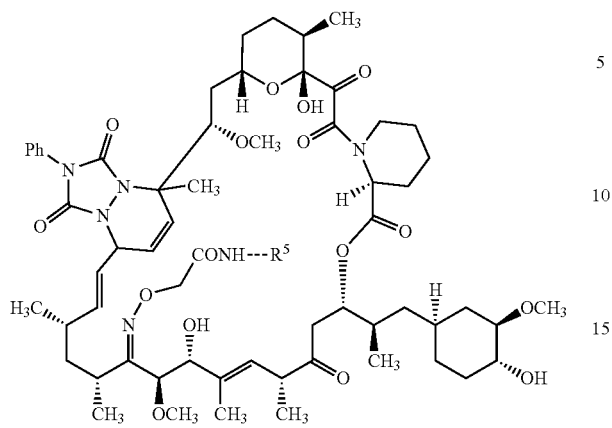
wherein R⁵ is BSA or KLH.
* * * * *

UNITED STATES PATENT AND TRADEMARK OFFICE
CERTIFICATE OF CORRECTION

PATENT NO. : 11,377,483 B2  
APPLICATION NO. : 17/247219  
DATED : July 5, 2022  
INVENTOR(S) : Yi Feng Zheng, Tie Q. Wei and Manoj Sharma Page 1 of 1

It is certified that error appears in the above-identified patent and that said Letters Patent is hereby corrected as shown below:

In the Claims  
Column 32, Lines 1-21, please delete the formula IIIa:

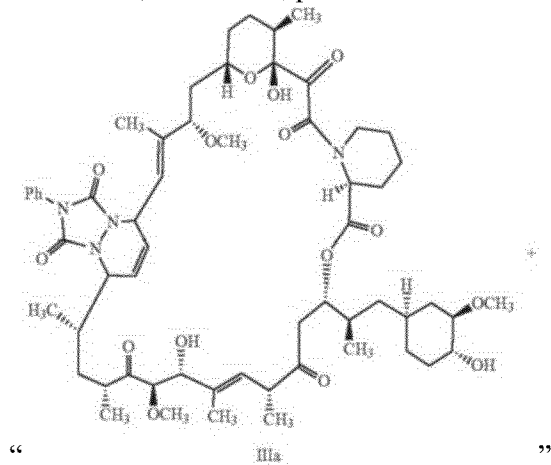

And replace with IIIa as shown below:

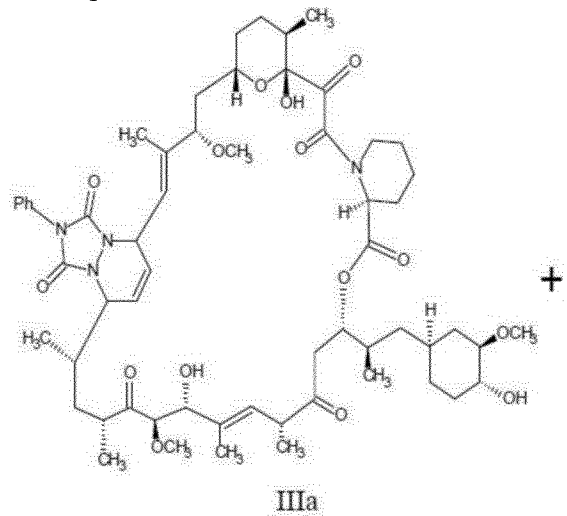

Signed and Sealed this  
Twenty-eighth Day of February, 2023

Katherine Kelly Vidal  
*Director of the United States Patent and Trademark Office*